United States Patent
Petterson et al.

(10) Patent No.: US 10,335,305 B2
(45) Date of Patent: Jul. 2, 2019

(54) SELF-ACTIVATED LIFTING VEST WITH SENSORY-FEEDBACK AND METHODS OF USE THEREOF

(71) Applicant: Strong Arm Technologies, Inc., Rochester, NY (US)

(72) Inventors: Sean Michael Petterson, Mount Sinai, NY (US); Justin Lamont Hillery, Rochester, NY (US)

(73) Assignee: Strong Arm Technologies, Inc., Rochester, NY (US)

( * ) Notice: Subject to any disclaimer, the term of this patent is extended or adjusted under 35 U.S.C. 154(b) by 525 days.

(21) Appl. No.: 14/780,110

(22) PCT Filed: Mar. 25, 2014

(86) PCT No.: PCT/US2014/031698
§ 371 (c)(1),
(2) Date: Sep. 25, 2015

(87) PCT Pub. No.: WO2014/160693
PCT Pub. Date: Oct. 21, 2004

(65) Prior Publication Data
US 2016/0038331 A1 Feb. 11, 2016

Related U.S. Application Data

(60) Provisional application No. 61/837,278, filed on Jun. 20, 2013, provisional application No. 61/809,342, (Continued)

(51) Int. Cl.
*A61F 5/02* (2006.01)
*A61B 5/11* (2006.01)

(52) U.S. Cl.
CPC ............ *A61F 5/026* (2013.01); *A61B 5/1116* (2013.01); *A61F 5/02* (2013.01); *A61F 5/028* (2013.01)

(58) Field of Classification Search
CPC .......... A61F 5/026; A61F 5/028; A61F 5/024; A61F 5/03; A61F 13/14; A61F 5/02; (Continued)

(56) References Cited

U.S. PATENT DOCUMENTS 1,581,791 A * 4/1926 Davison ................. A61F 5/026
2/331
5,256,135 A * 10/1993 Avihod ................ A61F 5/3784
128/874
(Continued)

FOREIGN PATENT DOCUMENTS

CN 1494403 5/2004
CN 1494405 5/2004
(Continued)

OTHER PUBLICATIONS

Chinese Office Action for Chinese Application No. 201480029879.0, dated Oct. 10, 2016 with translation, 13 pages.
(Continued)

*Primary Examiner* — Ophelia A Hawthorne
(74) *Attorney, Agent, or Firm* — Greenberg Traurig, LLP

(57) ABSTRACT

Medical lifting devices and methods are disclosed. A lifting support device includes a garment configured to be worn by a user and at least one sensory feedback element. The sensory feedback element is coupled to the garment and is configured to provide sensory feedback to the user. The sensory feedback encourages the user to adopt an appropriate posture during a lifting operation. A lifting vest includes a load transfer element, a posture compliance element, a coupling device, and at least one sensory feedback element. The load transfer element is configured to transfer a weight of a load to a point over shoulders of a user and down to a lower torso of the user. The posture compliance element is configured to passively or actively enforce an appropriate back posture. The coupling device is configured to connect the load-transfer element to the postural compliance element.

16 Claims, 28 Drawing Sheets

Related U.S. Application Data filed on Apr. 6, 2013, provisional application No. 61/804,785, filed on Mar. 25, 2013, provisional application No. 61/804,809, filed on Mar. 25, 2013.

(58) Field of Classification Search
CPC .......... A61F 5/30; A61F 5/058; A61F 5/0102; A61F 5/0193; A61F 2005/0155; A61F 5/055; A61F 5/34; A61F 2007/0024; A61F 2007/0228; A61F 2250/0004; A61F 5/3715; A61F 5/3784; A61B 5/1116; A41F 9/002; A41F 9/025; A41F 9/02; A41F 1/00; A41F 11/16; A41F 9/00; A41F 3/00; A41F 18/00
See application file for complete search history.

(56) References Cited

U.S. PATENT DOCUMENTS

| | | |
|---|---|---|
| 6,533,740 B2 | 3/2003 | Reinecke |
| 6,689,082 B2 | 2/2004 | Reinecke |
| 2005/0279791 A1* | 12/2005 | Komorowski .......... A45C 13/38 224/260 |
| 2006/0282032 A1* | 12/2006 | Smith ..................... A61F 5/026 602/19 |
| 2008/0228121 A1 | 9/2008 | Hughes |
| 2010/0204629 A1 | 8/2010 | Specht |
| 2012/0059297 A1* | 3/2012 | Newkirk ................. A61F 5/026 602/19 |

FOREIGN PATENT DOCUMENTS

| | | |
|---|---|---|
| KR | 20060001857 | 1/2006 |
| WO | WO 2012/135613 A2 | 10/2012 |

OTHER PUBLICATIONS

International Search Report for Application No. PCT/US2014/031698 dated Jul. 28, 2014.
European Office Action for European Application No. 14726458.4, dated Nov. 10, 2016, 3 pages.
International Preliminary Report on Patentability for International Application No. PCT/US2014/031698 dated Sep. 29, 2015.

* cited by examiner

SELF-ACTIVATED LIFTING VEST WITH SENSORY-FEEDBACK AND METHODS OF USE THEREOF

CROSS-REFERENCE TO RELATED APPLICATIONS

This application is a U.S. National Phase Application of PCT International Application PCT/US2014/031698 filed Mar. 25, 2014, which claims priority to U.S. Patent Application No. 61/804,785, entitled "SELF-ACTIVATED LIFTING VEST WITH SENSORY-FEEDBACK FOR INDUSTRIAL ATHLETES," filed on Mar. 25, 2013, and to U.S. Patent Application No. 61/804,809, entitled "SELF-ACTIVATED LIFTING VEST WITH SENSORY-FEEDBACK FOR INDUSTRIAL ATHLETES (WITH SUPPLEMENTAL DRAWINGS)," filed on Mar. 25, 2013, and to U.S. Patent Application No. 61/809,342, entitled "SELF-ACTIVATED LIFTING VEST WITH SENSORY-FEEDBACK FOR INDUSTRIAL ATHLETES AND HAND-EFFECTOR MEANS THEREOF," filed on Apr. 6, 2013, and to U.S. Patent Application No. 61/837,278, entitled "SELF-ACTIVATED LIFTING VEST WITH SENSORY-FEEDBACK FOR MEDICAL APPLICATIONS AND HAND-EFFECTOR MEANS THEREOF," filed on Jun. 20, 2013, the contents of each of which are incorporated herein by reference in their entireties.

FIELD OF THE INVENTION

The present invention preferably relates to a self-activated lifting vest with sensory-feedback or "LV(SF)" as conferred by at least one "sensory-feedback means" ("SF means") for use in appropriate lifting and/or medical applications, and more particularly, in medical lifting applications.

BACKGROUND OF THE INVENTION

According to the U.S. Occupational Health and Safety ("OSHA") technical manual, "back disorders can develop gradually as a result of microtrauma brought about by repetitive activity over time or can be the product of a single traumatic event . . . acute back injuries can be the immediate result of improper lifting techniques and/or lifting loads that are too heavy for the back to support." See OSHA technical manual, Section VII, Chapter I, "Back Disorders and Injuries," publicly available from OSHA's website. As the OSHA Manual then goes on to note, "although back injuries account for no work-related deaths, they . . . are one of the leading causes of disability for people in their working years and afflict over 600,000 employees each year with a cost of about $50 billion annually in 1991 according to NIOSH . . . [and] the frequency and economic impact of back injuries and disorders on the work force are expected to increase over the next several decades as the average age of the work force increases and medical costs go up."

Given the enormous health and economic consequences of lifting-related back injuries, there have been a large number of devices developed that purport to be useful for better lifting safety. See, e.g., the numerous examples of such devices within U.S. Classification Class/Subclass 602/19. However, in 1994 a "Back Belt Working Group" of the National Institute of Occupational Health and Safety ("NIOSH") reviewed commercially available lifting belts and concluded that such "back belts do not mitigate hazards to workers posed by repeated lifting, pushing, pulling, twisting, or bending" and that, in light of "insufficient data indicating that typical industrial back belts significantly reduce the biomechanical loading of the trunk during manual lifting," this working group concluded that 1) back belts are not recommended for preventing injuries; and, 2) back belts are not personal protective equipment ("PPE"). See NIOSH publication 94-122, publicly available from the website for the Center for Disease Control (CDC). See also NIOSH's 1996 summary of these results, NIOSH publication 94-127, October, 1996, publicly available from the CDC's website.

In light of the above health and economic consequences of lifting-related back injuries and the lack of suitable devices for preventing such injuries, there is a great need for the development of better lift-assistance devices.

SUMMARY OF THE INVENTION

Aspects of the present invention are directed to medical lifting devices and methods.

In accordance with one aspect of the present invention, a support device is disclosed. The support device comprises a garment configured to be worn by a user and at least one sensory feedback element. The sensory feedback element is coupled to the garment. The at least one sensory feedback element is configured to provide sensory feedback to the user. The sensory feedback is configured to encourage the user to adopt an appropriate posture during a lifting operation by the user.

In accordance with another aspect of the present invention, a lifting vest is disclosed. The lifting vest comprises a load transfer element, a posture compliance element, a coupling device, and at least one sensory feedback element. The load transfer element is configured to transfer a weight of a load from a location of the load to a point over shoulders of a user and down to a lower torso of the user. The posture compliance element is configured to passively or actively enforce an appropriate back posture. The coupling device is configured to connect the load-transfer element to the postural compliance element. The at least one sensory feedback element is configured to provide sensory feedback to the user.

In accordance with yet another aspect of the present invention, a method of creating appropriate lifting posture in an individual is disclosed. The method comprises enabling the individual to perform a lifting operation while wearing either the above-described support device or the above-described lifting vest.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. According to common practice, the various features of the drawings are not drawn to scale unless otherwise indicated. To the contrary, the dimensions of the various features may be enlarged or reduced for clarity. Included in the drawings are the following figures:

FIG. 18 provides a view with the softvest 1820 shown; FIG. 19 shows the same view but with the softvest 1820 removed for a clearer view. Note that for clarity FIG. 19 shows the right waist cord guide actually attached to the softvest 1820. Also note that, although the backplate 1810 in this and the other figures provided is shown as thinned in its middle portion, this is not the only contemplated form of the backplate 1810, and is explicitly not limiting of the backplate 1810 configuration (see, e.g., the alternate configuration of FIG. 24).

FIG. 21 shows the action of the sensory-feedback-means (backplate assembly 1800) to create sensory feedback for the user.

FIG. 23 shows an embodiment of the backplate assembly 1800 in the lower fulcrum 722 region, with an arrangement including an adjustable lower pad 2300 (e.g., adjustable using hook-and-loop fasteners 2310, with the direction of adjustment indicated by arrows 2320) that allows for precise placement of pressure exerted by the action of the LV(SF) with regard to the spine to create sensory feedback, e.g., in a preferred embodiment as the adjustment of the adjustable lower pad 2300 to press against the lower back in the L5/S1 spinal region. FIG. 24 provides various views at 1:4 scale of a preferred embodiment of the backplate assembly 1800, and shows the locations of both lower pad 2300 and upper pad 2400 where upper pad 2400 preferably is located so as contact the back in the thoracic region of the spine, i.e., circa T10-T12, and preferably T10.

DETAILED DESCRIPTION OF THE INVENTION

Figure 1:
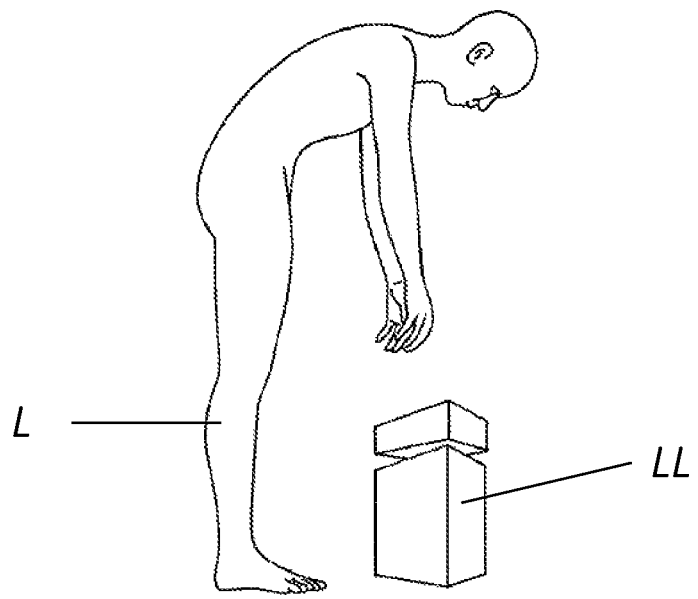
FIG. 1 provides a schematic example of non-ergonomic lifting, i.e., lifting by keeping the legs straight/locked and bending at the waist with a hunched back.

The present invention preferably relates to a self-activated lifting vest with sensory-feedback or "LV(SF)" as conferred by at least one "sensory-feedback means" ("SF means") for use by industrial athletes for appropriate lifting and/or for medical applications, including particularly medical lifting applications. The present invention is also directed to particularly preferred embodiments of this LV(SF), including particularly hand-effector means for use with this LV(SF) for use for medical lifting applications.

In this regard, medical lifting is a source of large numbers of back injuries to nurses and other hospital/medical personnel; in 2009 for example workers in this field reported the highest prevalence and most annual cases of work-related back pain involving days away from work in the Healthcare and Social Assistance Sector (HCSA) (see the "Safe Patient" page on the CDC website). The LV(SF) of the present invention is ideally suited to such applications, especially when the hand effectors are optimally adapted for such applications. Exemplars of such optimized hand effectors are provided below.

In embodiment 1, the present invention is directed to a lifting vest with sensory feedback ("LV(SF)") comprising at least one Sensory-Feedback means ("SF means") that provides sufficient Sensory-Feedback ("SSF") to result in the wearer adopting the appropriate posture during a percentage of his/her lifts.

In embodiment 2, the present invention is directed to the LV(SF) of embodiment 1, where the appropriate lifting posture is as defined by the Mayo Clinic on their website.

In embodiment 3, the present invention is directed to the LV(SF) of embodiment 1, where the SSF results in the LV(SF) wearer adopting the appropriate posture during lifting in at least 50% of the lifts performed by that individual wearer.

In embodiment 4, the present invention is directed to the LV(SF) of embodiment 1, where the SSF results in the adopting of the appropriate posture during lifting in at least an average of 50% of the lifts performed by a cohort (group) of LV(SF) users.

In embodiment 5, the present invention is directed to the LV(SF) of embodiment 1, where the SF is provided by inward pressure on the wearer's back.

Figure 21:
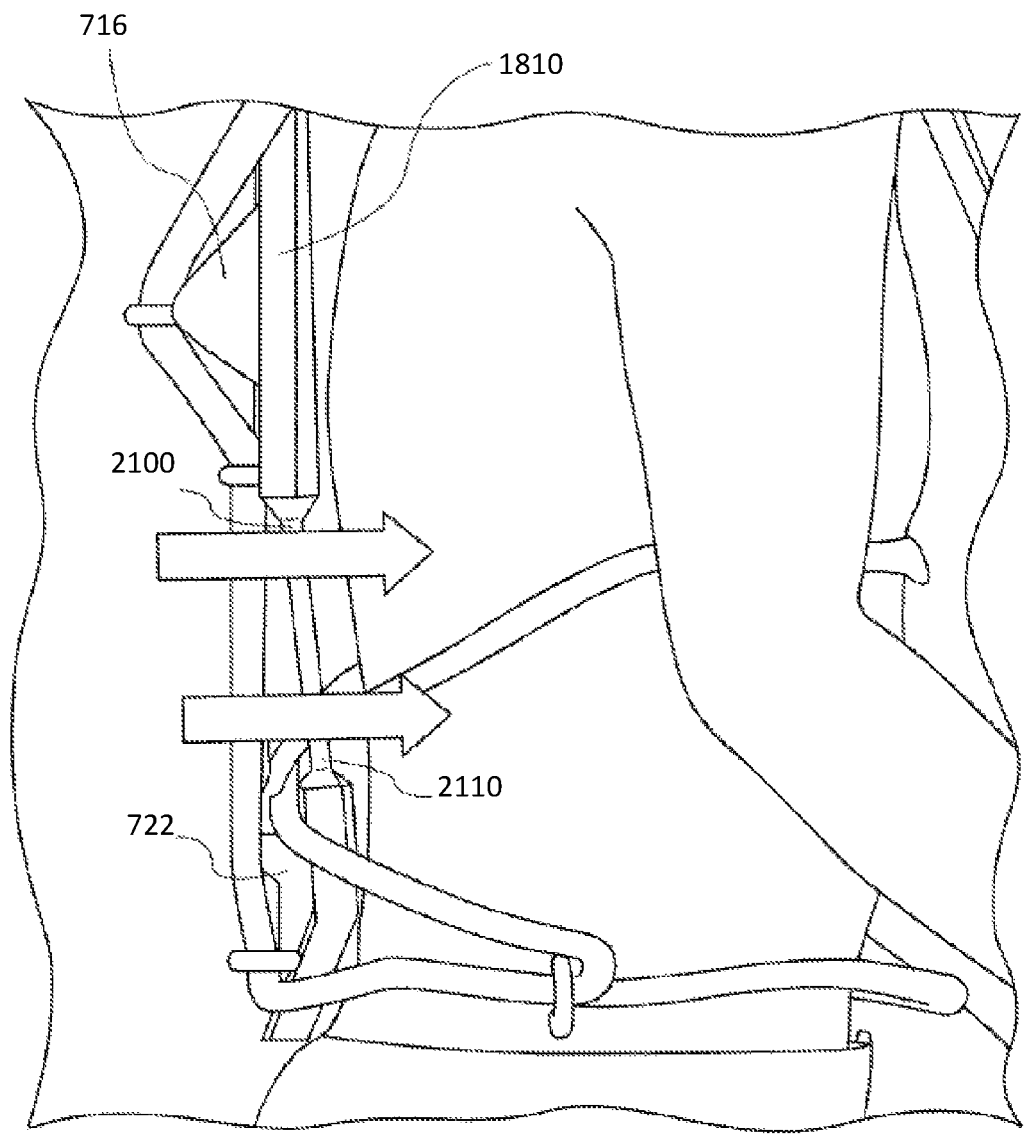
FIG. 21 provides a side view of the backplate assembly 1800 with the softvest 1820 removed for clarity of view. The arrows in this figure again show the motion of the backplate 1810 as a result of extension of the hands/cords. This figure also shows the pivot points 2100, 2110 in the backplate 1810 itself; note that this is only one configuration for such pivot points 2100, 2110, and is not intended to be limiting of these pivot points 2100. As for FIG. 20.
Figure 23:
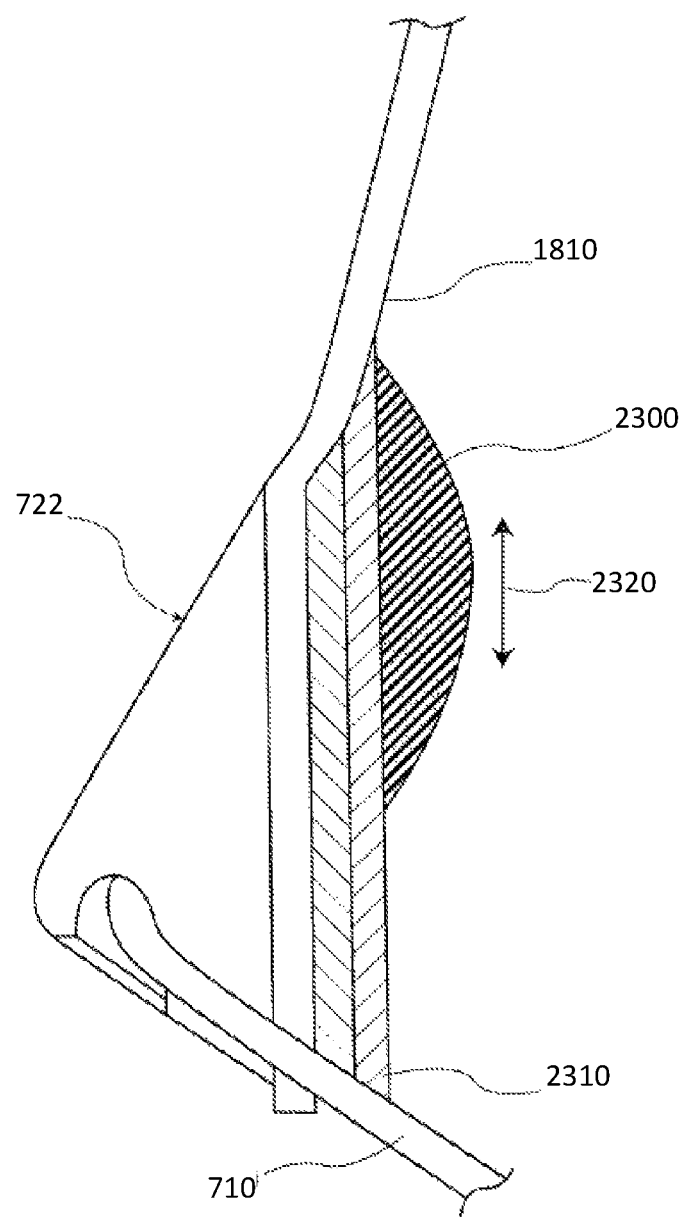
FIGS. 23-24 provide further details regarding a preferred embodiment of the backplate assembly 1800.
Figure 24:
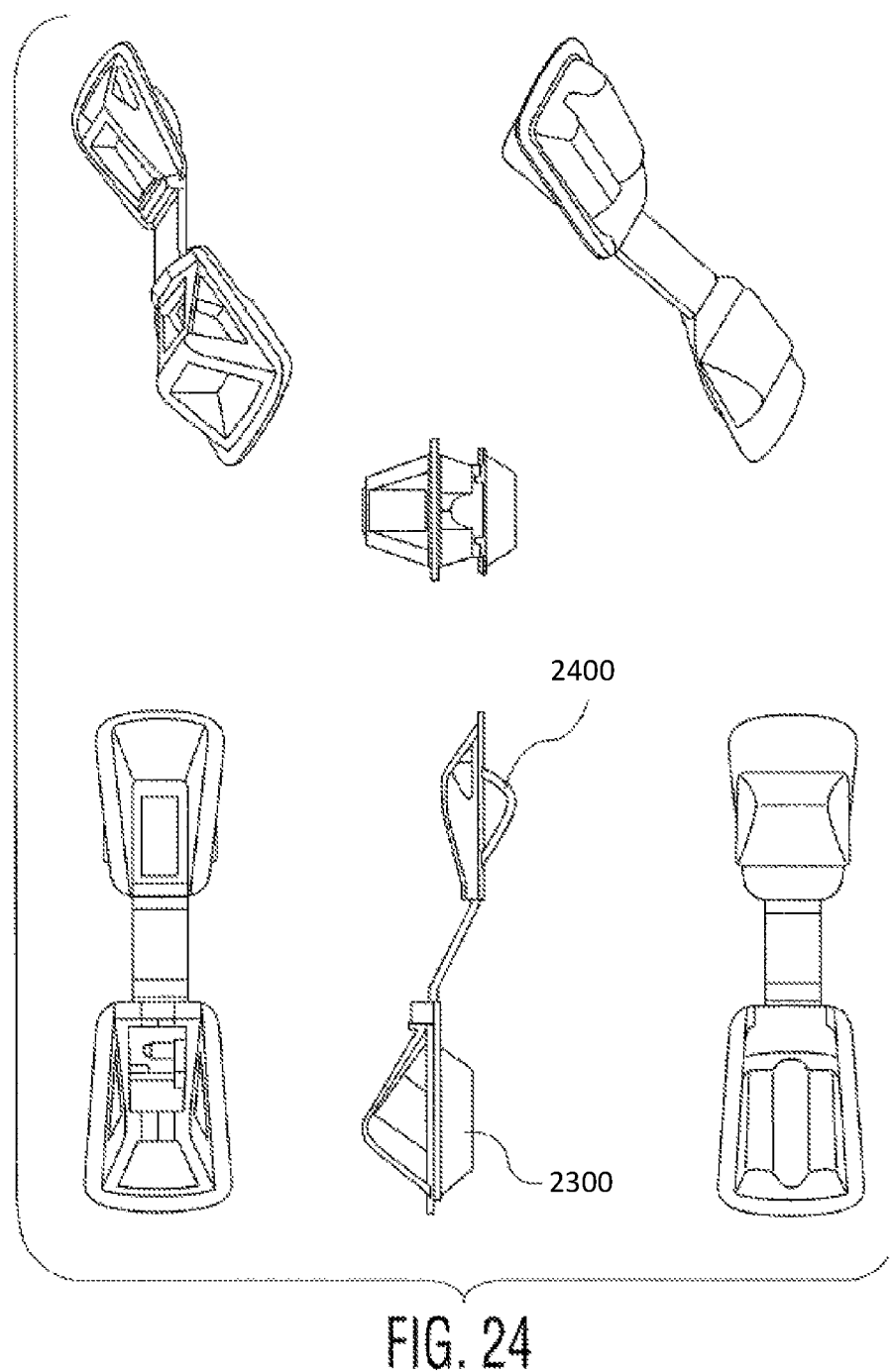

In embodiment 6, the present invention is directed to the LV(SF) of embodiment 1, where the at least one SF-means comprises the backplate assembly configuration of FIG. 21, FIG. 23, or FIG. 24, or a combination thereof.

In embodiment 7, the present invention is directed to a lifting vest with sensory feedback ("LV(SF)") comprising: i) a load transfer means ("LTM"), for transferring the load weighting from the lifting point over the shoulders and down to the lower torso; ii) a postural compliance means ("PCM"), for passively/actively enforces the appropriate back posture; and, iii) a coupling means ("CM"), for coupling increased loading on the load-transfer means into increasing engagement of the postural compliance means; and, iv) at least one Sensory-Feedback means ("SF means") for providing sensory-feedback (SF) to the LV(SF) wearer.

In embodiment 8, the present invention is directed to the LV(SF) of embodiment 7, where the SF means is integrated into the PCM.

In embodiment 9, the present invention is directed to the LV(SF) of embodiment 7, where the SF means provides SSF in at least 50% of the lifts performed by the LV(SF) user.

In embodiment 10, the present invention is directed to the LV(SF) of embodiment 7, where the SF is provided by inward pressure on the wearer's back.

In embodiment 11, the present invention is directed to the LV(SF) of embodiment 7, where the at least one SF-means comprises the backplate assembly configuration of FIG. 21, FIG. 23, or FIG. 24, or a combination thereof.

In embodiment 12, the present invention is directed to a method of creating appropriate lifting posture in an individual, comprising having the individual lift while wearing the LV(SF) of embodiment 1.

In embodiment 13, the present invention is directed to the method of embodiment 10, where the individual is selected from the group consisting of industrial athletes and non-industrial LV(SF) wearers.

In embodiment 14, the present invention is directed to a method of creating appropriate lifting posture in an individual, comprising having the individual lift while wearing the LV(SF) of embodiment 7.

In embodiment 15, the present invention is directed to the method of embodiment 10, where the individual is selected from the group consisting of industrial athletes and non-industrial LV(SF) wearers.

In embodiment 16, the present invention is directed to the LV(SF) of embodiment 1 or embodiment 7, where the LV(SF) is used for a medical lifting application.

In embodiment 17, the present invention is directed to the LV(SF) of embodiment 16, comprising the hand effector embodiment of FIGS. 28-33.

In embodiment 18, the present invention is directed to the method of embodiment 12, where the LV(SF) is used for a medical lifting application.

Figure 34:
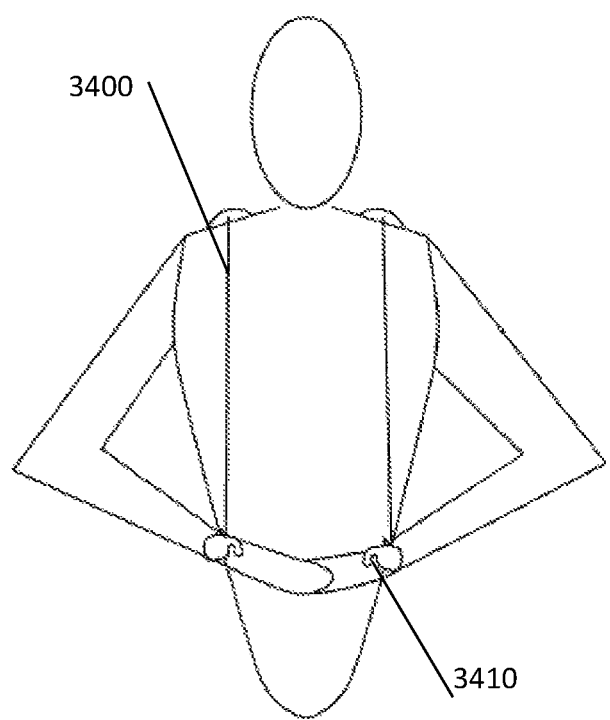
FIGS. 34-36 provide non-limiting but preferred embodiments of the medical lifting hand effector means of the present invention.
Figure 35:
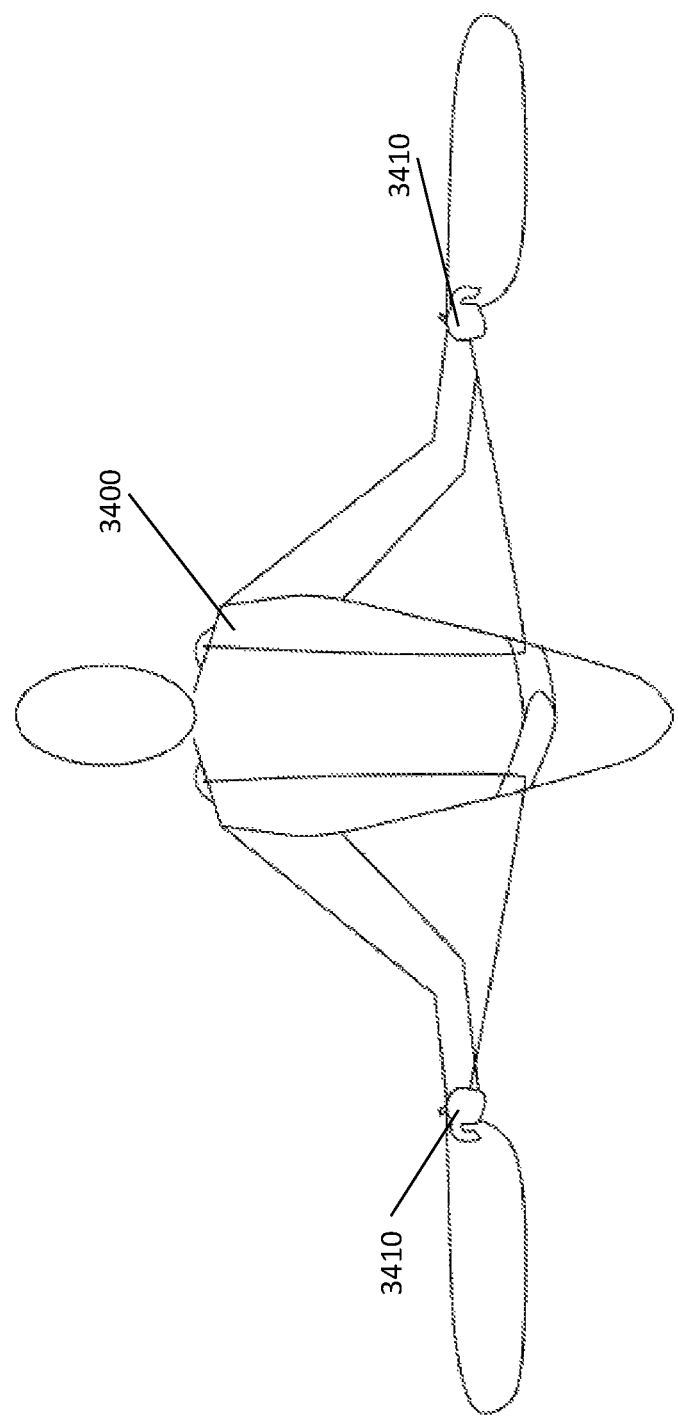
Figure 36:
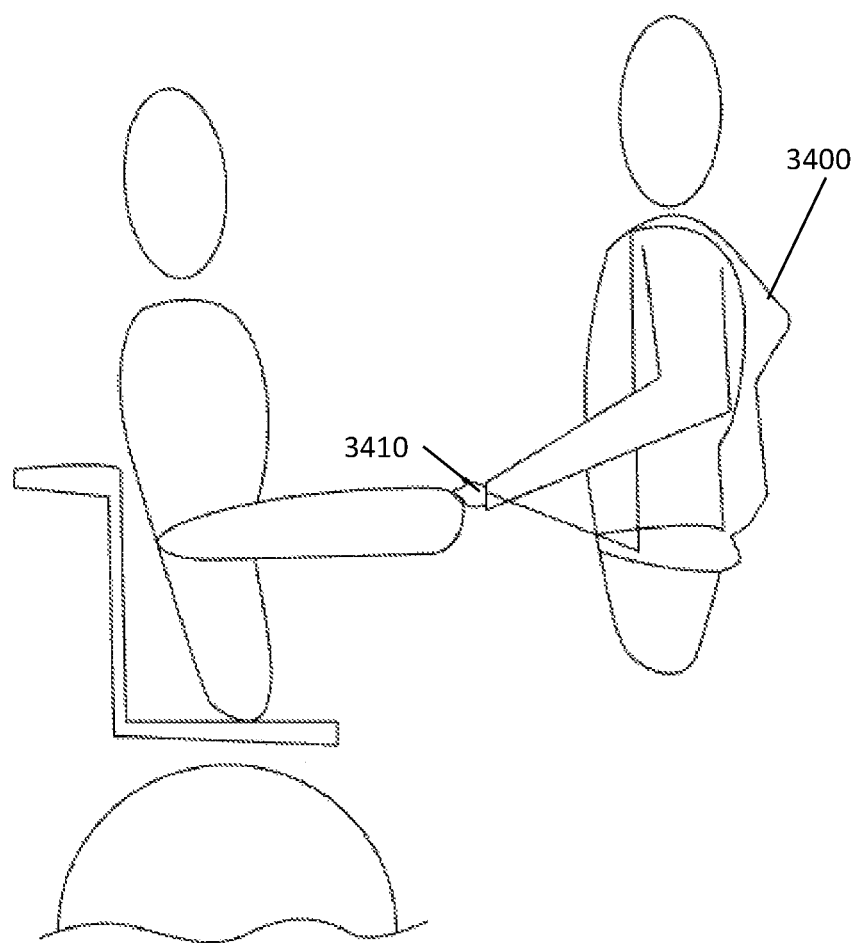

In embodiment 19, the present invention is directed to the method of embodiment 18, comprising the hand effector embodiment of FIGS. 34-36.

Applicants have previously filed U.S. patent application Ser. Nos. 61/516,277 and 61/595,187, and corresponding PCT/US2012/031440 (published as WO2012/135613), directed to "Self-Activated Postural Compliance Lift-Assistance Device" (all incorporated in their entireties by reference; also note that the basic LTM/CM/PCM terminology used in the present application explicitly refers to these components as defined in this earlier series of applications) that puts the wearer in an increasingly supported lifting posture, thereby providing a lift-assistance device that conforms with best ergonomic practices for lifting.

Appropriate Lifting Posture/Sequence of Lifting Postures

Aspects of the present invention are based on the recognition that lifting-related injuries can be significantly reduced by: 1) compliance with the appropriate sequence of postures during lifting; and, 2) mechanical distribution of weight across the body as determined by ergonomic studies. In order to implement 1) and 2) above the present invention is particularly directed to an unconventional device for insuring sequenced postural compliance and appropriate weight distribution, while also supplying a third critical factor of 3) a device design that is comfortably donned/removed and worn, in order to prevent user non-compliance, within 4) appropriate manufacturability parameters, e.g., durability and price.

With regard to the first factor, the appropriate sequence of postures during lifting, a large number of ergonomic studies have established a standard sequence of postures for lifting. The Mayo Clinic, for example, lists a lifting sequence consisting of 6 steps: 1) start in a safe position; 2) maintain the natural curve in your lower back; 3) use your legs; 4) squatting instead of kneeling; 5) let your legs do the work; and, 6) avoid twisting. This sequence of steps captures the two basic principles of a) not lifting at the waist, and instead b) lifting with the back relatively erect, using the legs. Thus as shown in FIG. 1, lifting by keeping the legs L straight/locked and bending at the waist with a hunched back is non-ergonomic lifting, since lifting in this posture forces the spine to support both the weight of the upper body and the weight of the load LL being lifted and, worse, the distance of the load out from the center of the body in this posture enormously increases the strain acting on the spine, e.g., into the thousands of foot-pounds of torque. See, e.g., "Biomechanics of Safe Lifting, available online at the publicly available website for Cornell University Ergonomics. See also, e.g., "Applications Manual for the Revised NIOSH Lifting Equation," 1994, NIOSH publication PB94-176930.

Figure 2:
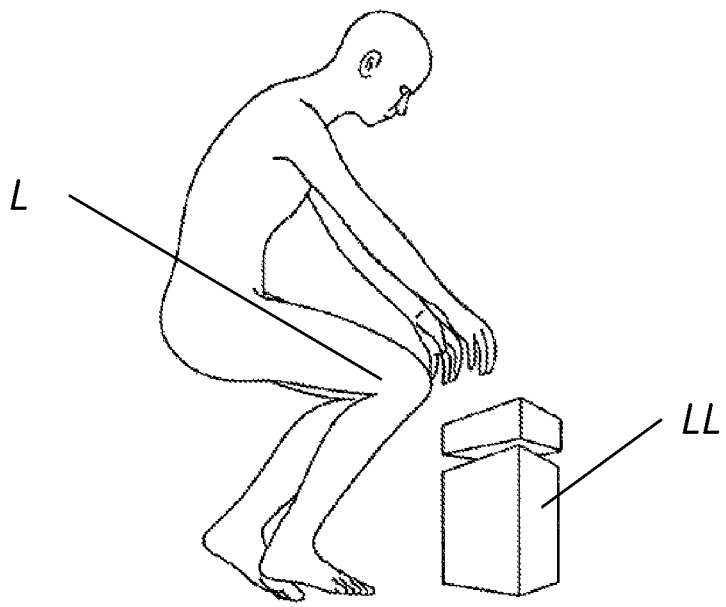
FIG. 2 provides a schematic example of ergonomic lifting, which involves keeping the weight as close to the body as possible, keeping the torso relatively erect to preserve the natural curvature of the spine, and using the leg muscles to do the lifting, e.g., by going from a squat to a standing position.

Instead, as shown in FIG. 2, ergonomic lifting involves keeping the weight of the load LL as close to the body as possible, keeping the torso relatively erect to preserve the natural curvature of the spine, and using the muscles of the legs L to do the lifting, e.g., by going from a squat to a standing position. In this regard, it is worthwhile nothing that, according to NIOSH1996, "[i]t would appear that abdominal belts help restrict the range of motion during side to side bending and twisting. However, they do not have the same effect when the worker bends forward, as in many industrial lifting situations." Thus it would appear that current support belts generally have little if any effect on ensuring this correct lifting posture and, as a result, a worker wearing a conventional lifting belt is unlikely to adopt this posture—keeping the weight close to the body by minimizing bending from the waist (thereby keeping the torso upright and lowering the stresses on the spine)—or the coupled requirement for proper lifting of using the legs to lift, i.e., by going from a squat to an erect position during lifting.

The Lift-Assistance Device of the Present Invention

In this regard, one aspect the present invention is directed to ensuring that a wearer appropriately lifts loads 1) with the back in a series of positions that—as the loading increases—becomes increasingly constrained to be erect (i.e., a "self-activated" device), thereby ensuring that the user's spine experiences minimized loading during lifting and particularly when lifting the full load. A simple mechanical device for achieving this purpose might consist of two straps attached at a waist belt and going over one or more—and preferably both—of the two shoulders down to the weight being lifted in front, with the distal (far) ends of these straps ending either at the hands or in hooks or other grips that directly contact the weight being lifted. As long as the wearer keeps his/her back relatively erect, increasing loading on the two straps will pull the user further upright, that is, into the appropriate conformation for lifting.

In reality, a device as simple as that described above will not function appropriately because the user will naturally tend to hunch over, thereby worsening the wearer's posture and putting even greater loading on his/her spine.

Figure 3:
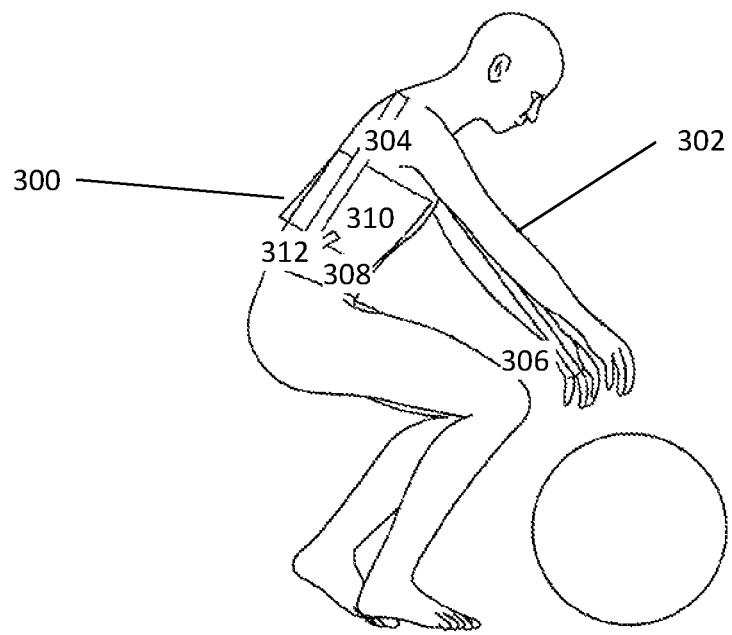
FIG. 3 provides a generalized schematic example of an embodiment of the invention in which the "load-transfer means" LTM (e.g., cords/straps S1 and S2) transfers the load from the lifting point over the shoulders and down to the "waist belt" W, where the weight is then transferred via "coupling means" C to the "postural compliance means" PCM, which upon increased loading increasingly engages to ensure the appropriate lifting posture of a non-loaded curve of the spine and prevents/enforces non-hunching.

FIG. 3 shows a more generalized schematic representation of one embodiment of the present invention, where the straps 30 and 32 (only 32 is shown; 30 is the mirror image of 32, in that it attaches in the region of the right hand and crosses the left shoulder in this criss-crossed 30/32 embodiment) ascend from an attached positioning at the "lifting point" in the region of the lower forearm/hands (e.g., by "lift coupling means" such as gloves, lifting hooks, wrist-straps, etc., as described in more detail below), over the shoulders (in either crossed or uncrossed conformations) and down across the back to the waist belt 34, where the straps are connected via coupling means 36 (here on each side of the body) to the postural compliance means 38 of the apparatus. In this representation, the coupling means 36 for each strap 30 and 32 could be a D-ring coupling means, although other coupling means are contemplated (see below). The postural compliance means 38 could be, e.g., straps that compress the torso upon loading of the straps, although this is only one of the embodiments contemplated for the postural compliance means 38.

Figure 7:
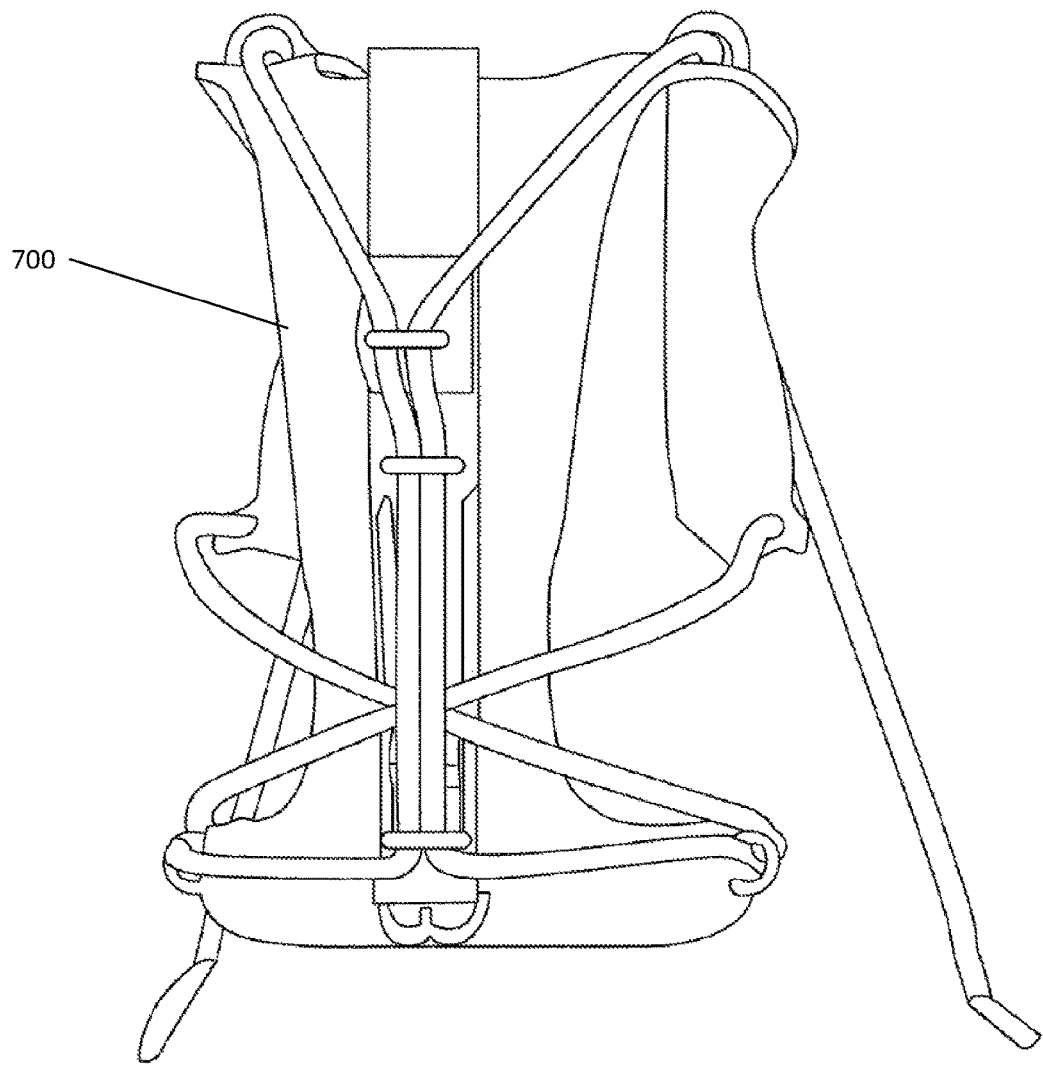
FIG. 7 provides a preferred embodiment of the LV(SF) device 700 of the present invention. Note the specific crossing of the back cords in this preferred embodiment.

Thus in the embodiment 300 depicted in FIG. 3, there are three critical sections to the embodiment: 1) the load-transfer means "LTM") 302, e.g., straps 304 and 306 (although the term "LTM" encompasses fewer or more straps, non-strap means such as ropes or strings, etc.), which transfers the load weighting from the lifting point (hands, wrists, forearms, etc.) over the shoulders and down to the lower torso, typically the waist belt 308 (again, the invention most generally contemplates one or more attachment points on the torso, preferably the lower torso, and still more preferably in the waist region); 2) the postural compliance means 310, which upon increased loading increasingly engages to ensure the appropriate lifting posture of a non-loaded curve of the spine and prevents/enforces non-hunching; and, 3) coupling means 312 (multiple coupling means are shown in this figure, but other numbers of such coupling means are contemplated, as in, e.g., FIG. 7), which allows increased loading on the LTM 302 such as 304/306 to be translated into increasing engagement of the 310 and, therefore, increasing postural compliance.

Figure 4:
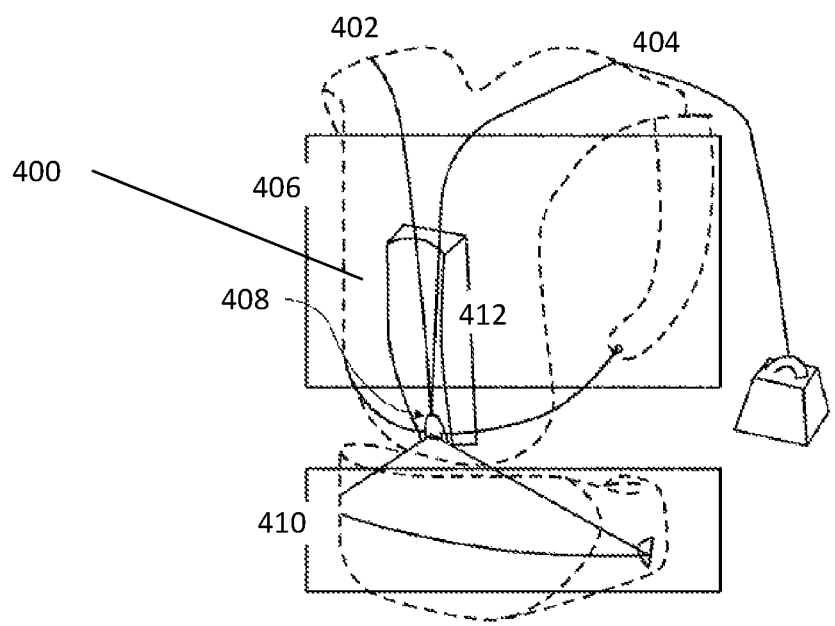
FIGS. 4-6 provide schematics of specific embodiments of the invention first disclosed in Applicants' earlier series of patent filings. In the embodiment of FIG. 4, for example, there is a single coupling means C that rides in a vertical channel in slide SL, where motion of C vertically in the channel of slide SL results in the coupling of increased weight on the load-transfer means LTM to increasingly enforced postural compliance via tightening of the PCM.
Figure 5:
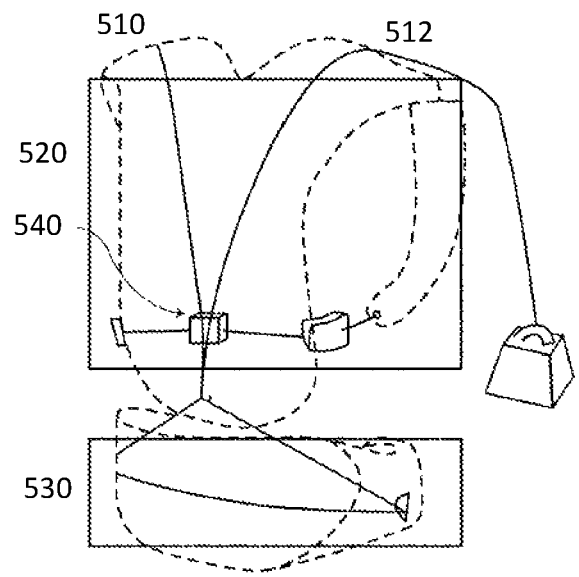
Figure 6:
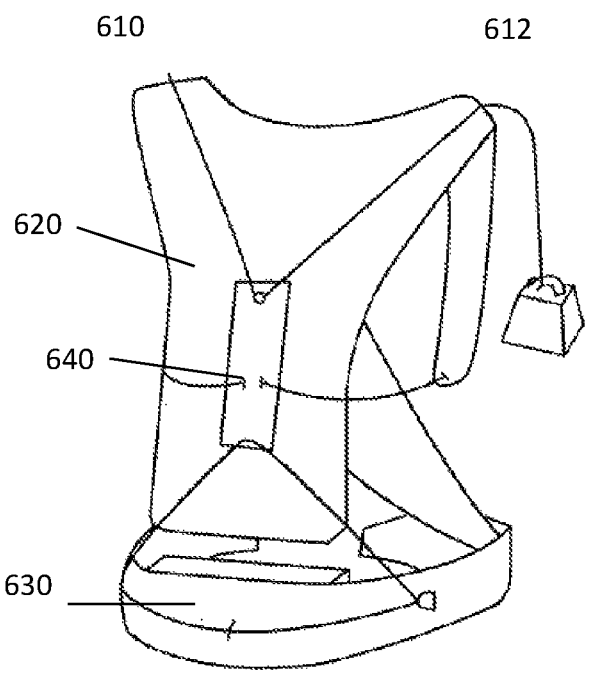

FIG. 4 shows a different embodiment 400 of the invention with load-transfer means 402 and 404, PCM 406, coupling means 408, and waist belt 410 operating as described above. In this embodiment there is a single coupling means 408 configured to slide up and down along a channeled slider 412 that is placed approximately mid-torso over the spine; as this coupling means 408 ascends the channel as a result of the downward motion of the load-transfer means 402 and 404 at their attachment points to the load (show in the figure as a rectangular weight with a handle attached to the "right" LTM 404 (i.e., the LTM 404 that descends to the wearer's right hand); the corresponding weight on the left LTM 402 is not shown), the postural compliance means 406 compresses the torso—in this embodiment via the drawing in of the shoulder straps—to the appropriate lifting posture. FIGS. 5 and 6 show additional exemplary embodiments 500 and 600, respectively, of the present invention, all of which embody the same basic principle of coupling between lifting using LTM 510, 512, 610, 612, the PCM 520, 620, and the waist belt 530, 630 via a single coupling means 540 or multiple coupling means 640. As discussed above, as loading on the load-transfer means LTM 510, 512, 610, 612 increases, so too does the postural compliance exerted by the postural compliance means PCM 520, 620, with the coupling between the two obtained by at least one coupling means 520, 620.

With regard to the change in the postural compliance enforced by the PCM, this change can be linear, or it can be non-linear. Thus for example the PCM may be gradually engaged via increased tensioning of straps; alternatively the PCM may be designed so that the PCM engages as an full-off or full-on process when sufficient lifting weight in the LTM.

Sensor-Laden Lift-Assistance Device

In additional embodiments, the present invention is directed to a lift-assistance device or vest that includes feedback sensors to indicate directly to the user, or by telemetry to a telemetry-storage device or remote telemetry network various data on user lifting.

Thus for example, in one embodiment, the lift-assistance device of the invention includes "unsafe weight" mechanical sensors that trip to indicate to the user that a weight outside of safe-lifting parameters is being lifted. Thus in one non-limiting embodiment, each LTM may have installed in it a mechanical device that, upon sufficient weighting, elongates with a pronounced noise, or that, upon elongation, exposes a colored "weight exceeded" color, or some combination of these indicators, to indicate to the user that the weight being lifted is unsafe for that user. Note that this "unsafe weight" may be a fixed weight, or it may be a weight that varies as a function of time-of-day, amount of weight already lifted by the user over the course of the day or in the last time period, some combination of the above, etc. Although the present invention contemplates unsafe weight sensors as typically being mechanical in nature, sensors that similarly signal unsafe weight using electrical means are also explicitly contemplated.

In other embodiments, the on-vest/on-body sensor(s) may transmit load/elongation data from multiple points on-vest/on-body, where such transmission is either wired or, preferably, wireless (e.g., by Bluetooth) to an on-body recording device, an on-body indicator/retransmission device (e.g., a smartphone application), an off-body receiver network, or some combination of the above. Intermittently- or continuously-transmitted data of this sort may be collected for a variety of purposes, including a) feedback to the vest-wearer regarding appropriate load lifting over the course of the day (e.g, as estimated by one or more algorithms regarding user capacity for additional lifting given previous lifts, time of day, state of body, etc.); b) data collection regarding lifting for correlation with injuries (i.e., to collect data for the development of safer-lifting algorithms); c) data collection for employer implementation of optimized worker lifting (e.g., real-time redistribution of workers based on metrics of each worker's approach to maximum lifting per day, per hour, etc., so that efficiency is maximized while likelihood of worker injuries is minimized by ensuring workers are not being overtasked for lifting). The present invention includes not just the hardware required for such implementations, but also the associated software, including software for a) data acquisition and processing; b) data-mining to extract safe lifting algorithm(s); data processing to coordinate workers, with additional software layers to ensure masking of data or other individual privacy layers to ensure protection of employees from inappropriate employer monitoring, etc.

Sensory Feedback Aspects of the Present Invention

Aspects of the present invention are also based on the unexpected discovery that lifting-vest-wearer compliance with appropriate lifting posture (the posture of FIG. 2) is obtainable largely if not entirely through sensory feedback, rather than by enforced compliance. That is, Applicants have discovered that worker adoption of the appropriate lifting posture is largely if not entirely obtainable by providing a vest that provides sensory feedback to the worker via at least one sensory-feedback means to indicate whether or not he/she is in the right posture.

Figure 20:
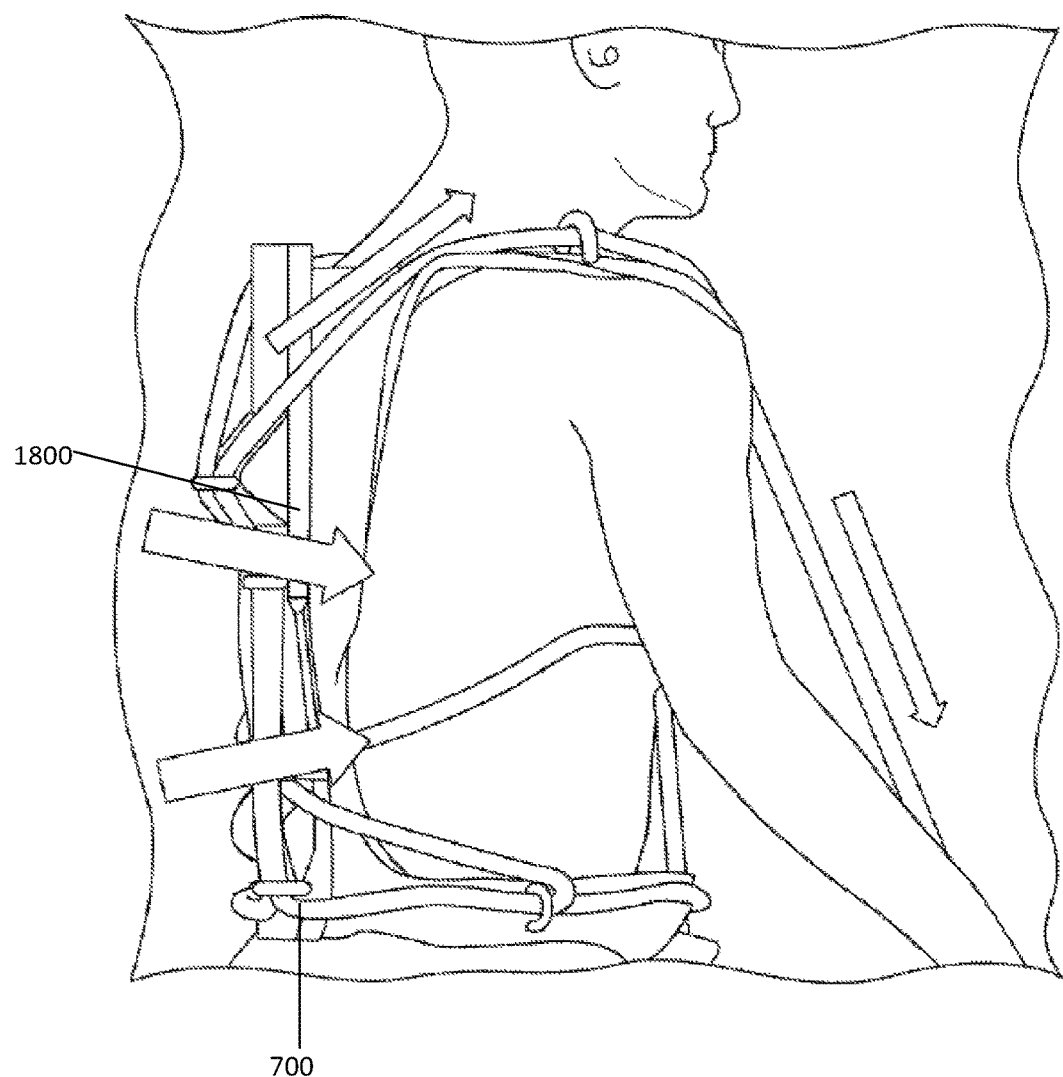
FIG. 20 provides a view of the preferred LV(SF) 700 of the present invention with thin arrows added to show the direction of motion of the cordage and thick arrows showing the resulting motion of the backplate assembly 1800 in towards the spine to create sensory feedback (SF).
Figure 22:
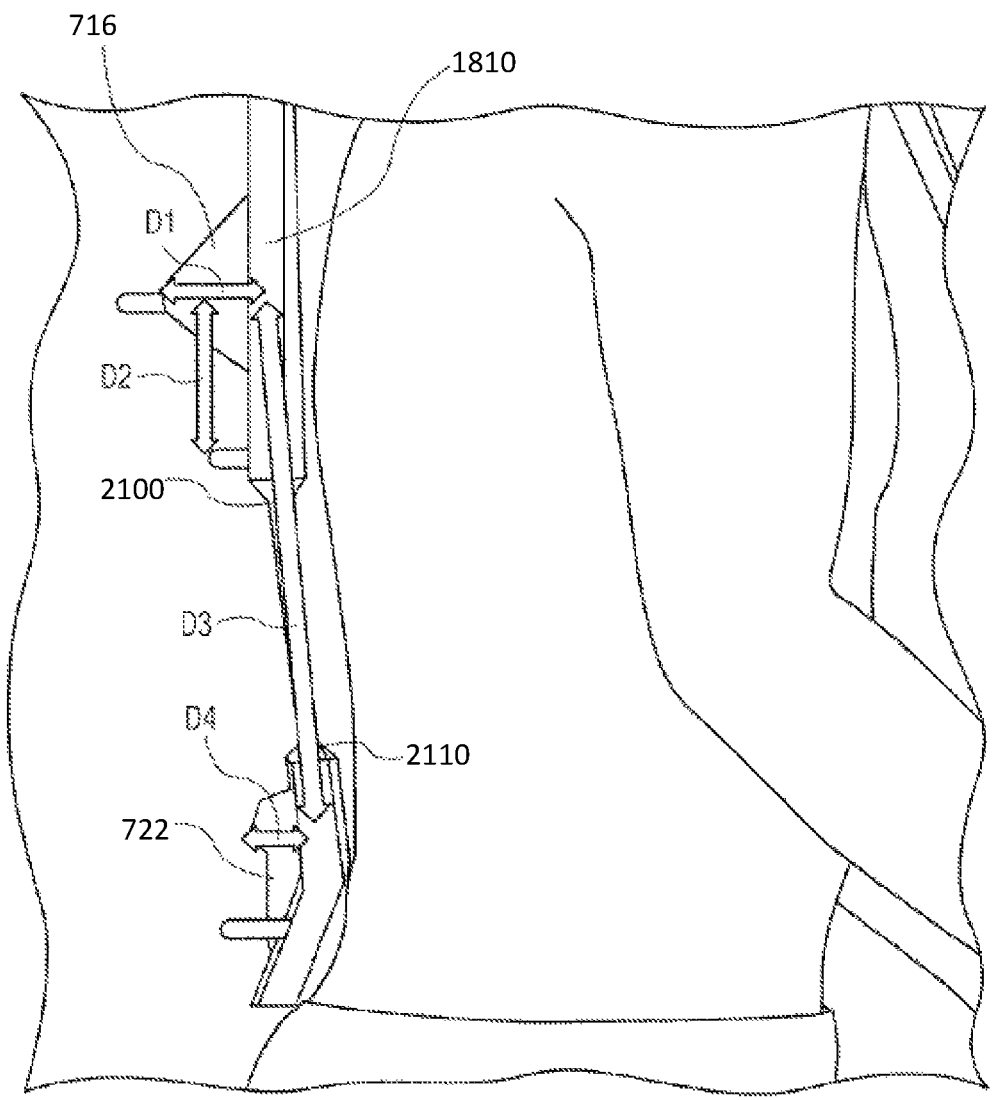
FIG. 22 provides a preferred backplate assembly of the present invention, with arrows indicating the height of the upper fulcrum 716 at its thickest point relative to the center of the backplate 1810 (length D1); the distance from the center of the upper fulcrum 716 to the central cord guide 718 (length D2); the distance between the cord-crossing-points of the upper and lower fulcrums 716, 722 (D3); and, the height of the lower fulcrum 722 at its thickest point relative to the center of the backplate 1810 (D4). Note that, although this figure does not provide arrows to show placement distances for the upper and lower pivot points 2100, 2110 relative to other backplate landmarks, Applicants explicitly contemplate variations in pivot point placements, and such variations may be measured relative to any of the indicated landmarks, and particularly relative to the upper fulcrum 716 for the upper pivot point 2100 (or pivot region) and the lower fulcrum 722 for the lower pivot point 2110 (or pivot region).

FIGS. 20 and 21 show a preferred embodiment of this sensory feedback principle, with the thick arrows in these figures showing that, as the vest is engaged, the backplate assembly 1800 (generically, sensory-feedback means) comprising back plate 1810 with pivot points 2100, 2110, upper fulcrum 716, lower fulcrum 722 and cord guides 712, 714, 718, 720, 724 (see FIGS. 22 and 9 for detailed renderings) moves so as to press into the wearer's back at the region shown, with this pressure providing sensory feedback to the wearer to adopt a more erect posture rather than the hunched over (incorrect) lifting posture of FIG. 1. Note that Applicants explicitly contemplate a number of different embodiments of this backplate assembly 1810 that are capable of imparting the appropriate sensation(s) to the wearer to trigger sensory-feedback on the wearer's part. Thus for example, FIG. 22 provides for varying distances between the components shown comprising his particularly preferred embodiment of the present invention (e.g., lengths D1-D4), and FIGS. 23-24 show various details of a preferred backplate assembly 1810 configuration including detail on the exemplary placement of the lower pad 2300 and upper pad 2400 that are an aspect of the preferred invention. All of these various configurations are exemplars of sensory-feedback means, as contemplated herein. Note that the particular thinning of the backplate shown in the backplate 1810 in the CG-modeled figures is only one contemplated configuration, and that appropriate pivot points 2100, 2110 may also be obtained by other means, such as specific backplate design(s) to introduce the requisite flexion (pivot) at the appropriate locations in the backplate 1810. See, e.g., the specific backplate assembly 1800 configuration of FIG. 24. Note also that the fulcrums 716, 722 shown in the figures are intended only as representative embodiments and do not represent the exhaustive set of fulcrums contemplated.

Applicants note that sensory-feedback-based postural response was not an expected outcome, and that, for example, standard back-braces and other lifting-aid devices do not provide for self-compliance by the user. In this regard Applicants note that part of the reason for this unexpectedness may be that devices developed for, e.g., industrial workers (a preferred, albeit non-limiting population of users of the present invention) are more typically safety devices, rather than the kind of high-tech equipment that competitive athletes now use, devices in which—seen from the vantage-point of post-inventive retrospect—sensory feedback is often an integral (if not explicitly described) part of the design. Thus industrial workers are—again in retrospect—conceptually put in a different category of non-athletes, with the result that some of the high-performance features of gear designed explicitly for ultra-athletes are not contemplated for inclusion in devices built for (in retrospect) equally as athletic industrial workers.

Although nothing in the preceding paragraph should be taken as a limiting theory for the unexpected discovery of the importance of sensory feedback for what Applicants now refer to as "industrial athletes" (again, the preferred but non-limiting user of the present invention), the result of this discovery as embodied in, for example, the sensory-feedback actions of the LV(SF) device shown in detail in FIGS. 20 and 21, provide a powerful approach to obtaining better lifting posture adoption by, e.g., industrial athletes.

Metrics for Sufficient Sensory Feedback

The present invention is explicitly directed to a lifting vest that provides sufficient Sensory-Feedback (SF) to create adoption of the appropriate lifting posture by the user. In this regard, SF is generated by at least one SF means, as discussed elsewhere. "Sufficient SF" (SSF) as used herein refers to SF sufficient to encourage appropriate lifting posture in a predetermined percentage of the number of lifts performed by an individual (e.g., 50% or more). Alternatively, the term may apply to such percentage as determined across a population of lifters. In another non-limiting embodiment, the term is contemplated as being measured by the actual force applied by the SF-means, by the resulting deformation of the back/spine, etc.

In this regard, Applicants note that yet another way of judging sufficient SF would be to determine the reduction in back injuries resulting from the particular LV(SF) embodiment, increased worker productivity, or other health/safety metrics.

The LV(SF) Device of the Present Invention—Additional Aspects

Figure 25:
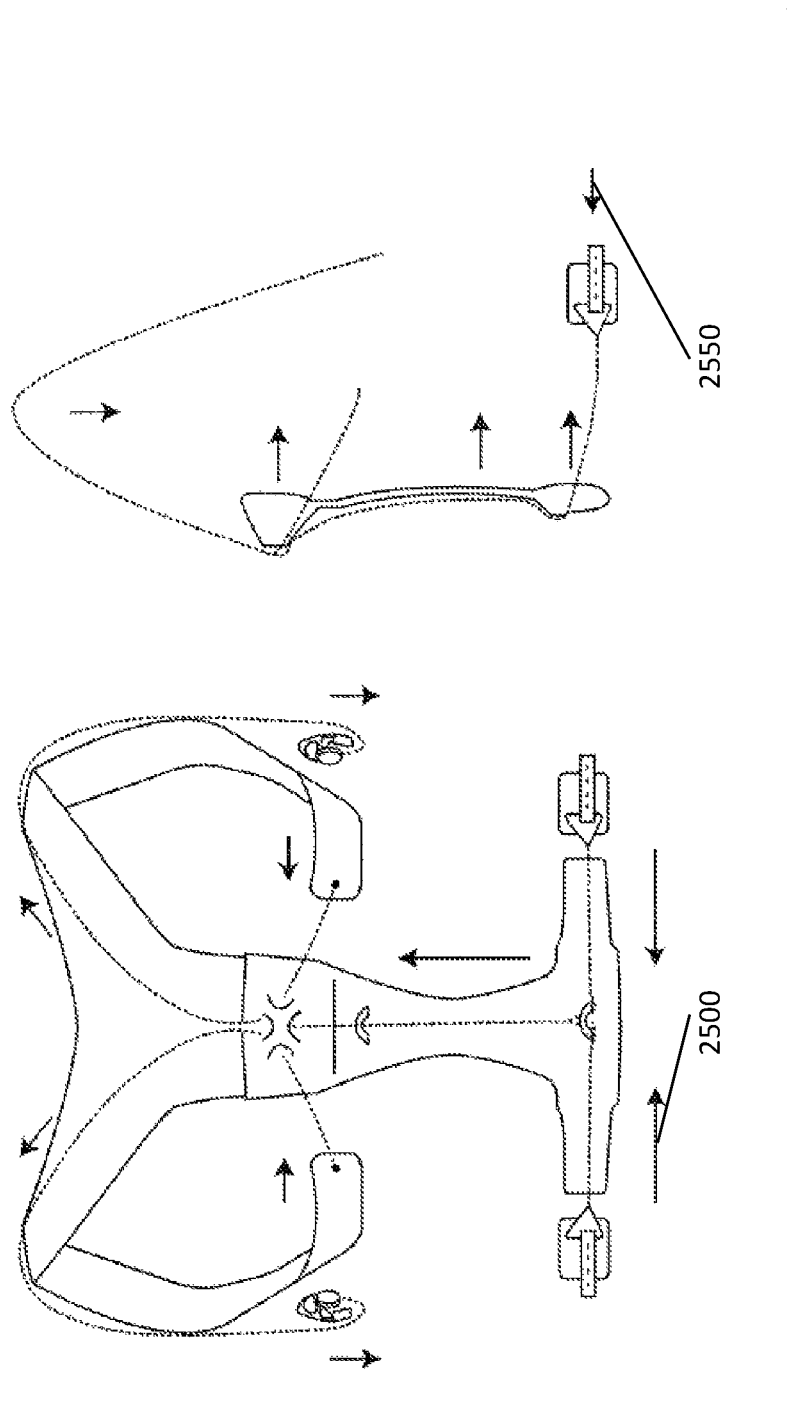
FIG. 25 provides schematics showing the motions of the cords 2500 (left panel) and resulting forces 2550 (right panel) that occur upon engagement of the LV(SF) device of the present invention to create sensory feedback. This figure shows a device embodiment corresponding to the VAR1 back cord embodiment, but the motions and forces are similar for the preferred embodiment, VAR2, and the other embodiments that, while contemplated, are not shown explicitly in the preferred, VAR1 or VAR2 embodiments.

Although a particularly preferred embodiment of the LV(SF) device of the present invention is directed solely to the inclusion of the sensory-feedback (SF) resulting from the inward motion of the appropriate region of the backplate (see previous section), the present invention is broadly directed to an invention that combines this SF-function with various other lifting vest functionalities to obtain the final LV(SF) product. FIGS. 7-9, 13-15, and 18-21 for example, explicitly show an additional preferred feature of cords crossing in the back in order to tighten the LV(SF) in around the torso as the hands are extended (see arrows in FIG. 8). Although such crossed cords are preferred, other embodiments for cord arrangement are explicitly contemplated, as shown in, for example, the non-limiting embodiments of FIGS. 10-12 and 16-17. Note that the schematic configuration of FIG. 25 is not intended to preclude any of these embodiments, but rather provides simply a schematic view of one particular embodiment.

Applicants note that a particularly preferred embodiment of the present invention combines the SF aspect with the load-transfer aspect (i.e., mechanical redistribution of weight across the body) obtained by the cordage (or alternatively, straps or other LTM) arrangements, some of which are shown in the accompanying figures.

Figure 27:
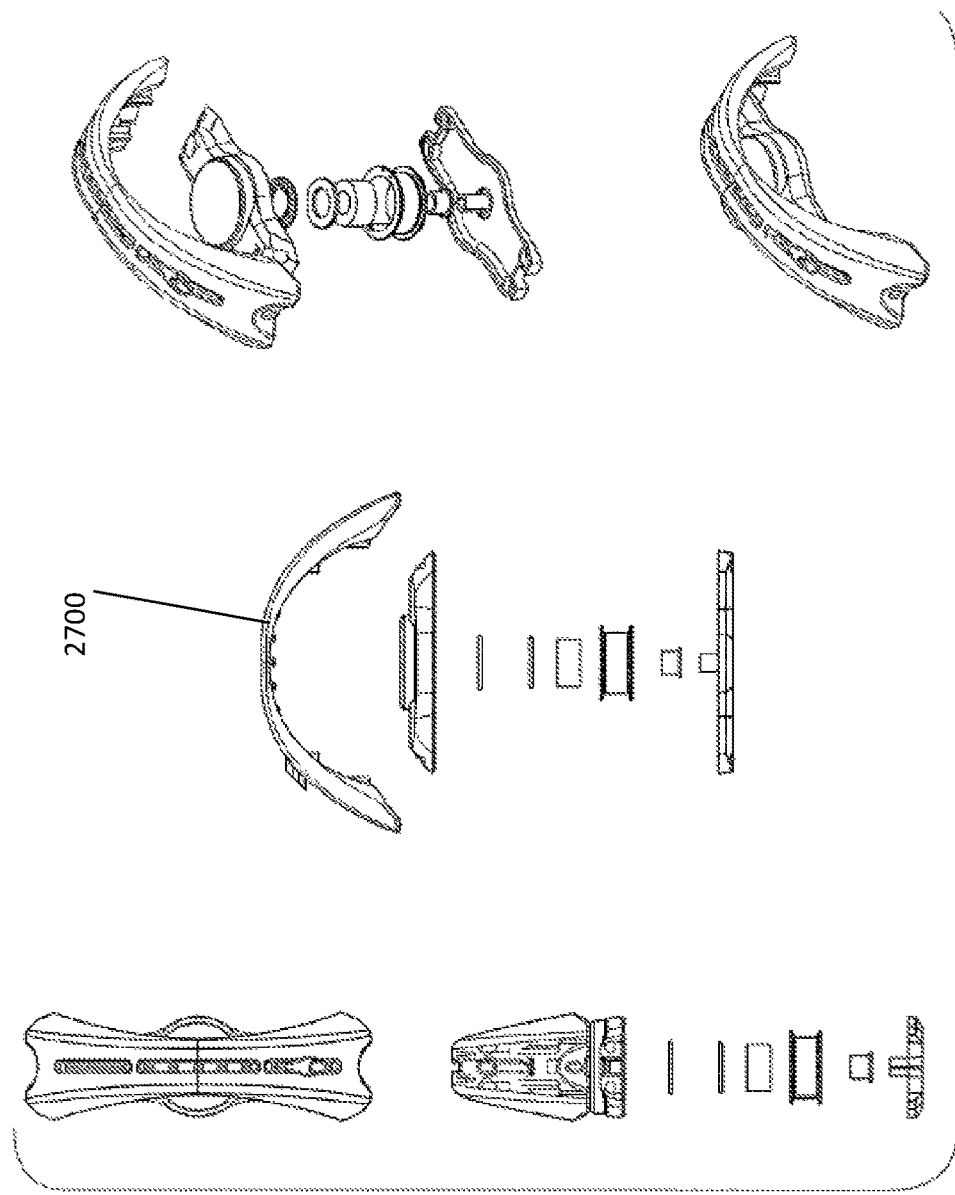
FIG. 27 provides a non-limiting but preferred embodiment of a retraction device in accordance with aspects of the present invention.
Figure 28:
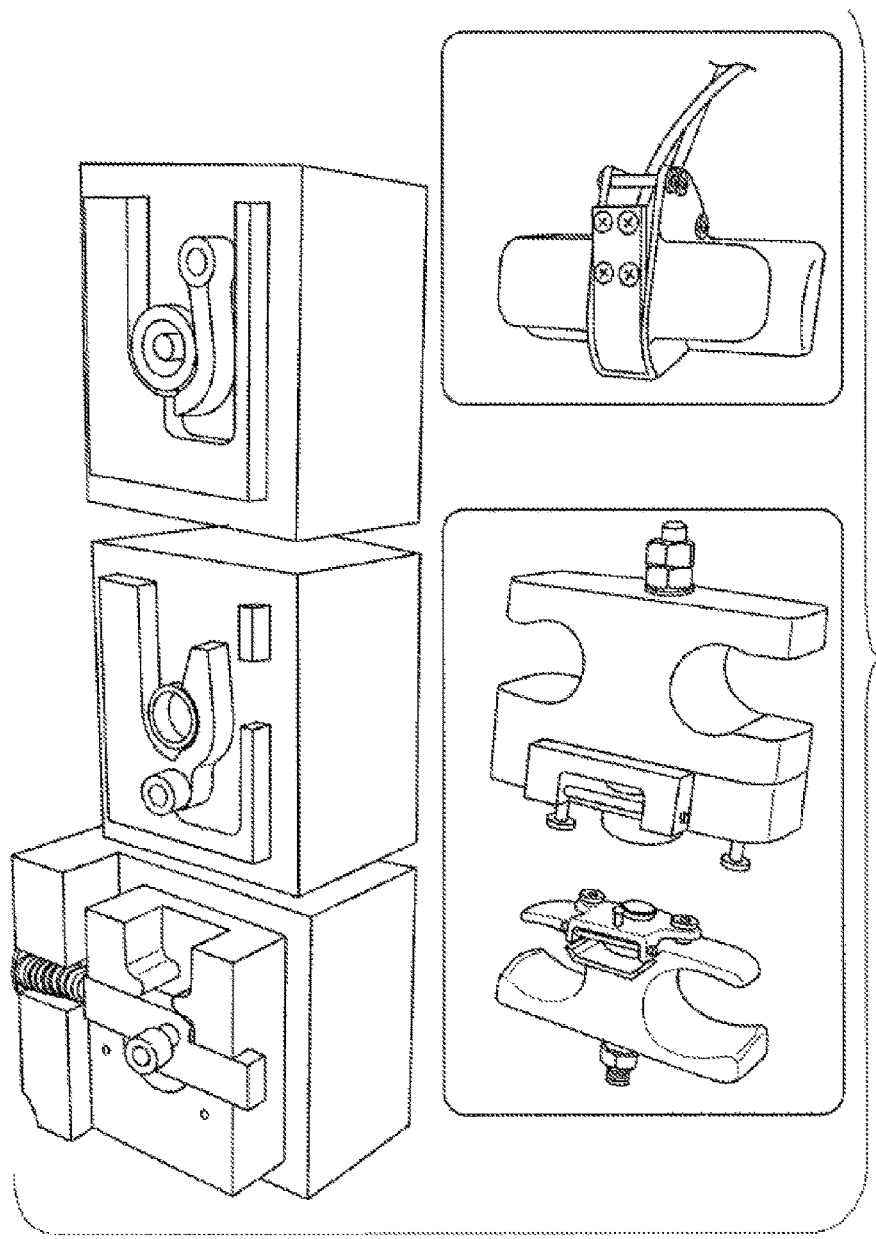
FIGS. 28-33 provide a non-limiting but preferred embodiment of the hand-effector means of the present invention.

The cords may be connected to a retraction device 2700, as shown in FIG. 27. The retraction device 2700 is coupled to the lifting vest such that it retracts the cords when they are not in use. In particular, the retraction device 2700 is configured to retract the cords from a first use position to a second standby position. Preferably, the retraction device 2700 automatically retracts the cords when the vest is not in use.

In a particular preferred embodiment, the cords are attached to elastic members (such as torsion springs) attached to the back of the lifting vest. The torsion springs are mounted along a plane substantially orthogonal to the plane of the user's back, in order to provide a desired retracting force on the cords. The retraction device may also comprise one or more pulleys coupled to the lifting vest. In this embodiment, the cords run along pulleys. When the cords are not in use, the pulleys apply a force to the cords that causes them to retract into the standby position.

Variants of Cords/Cord Guides/Softvest and Other Components of the LV(SF)

Figure 26:
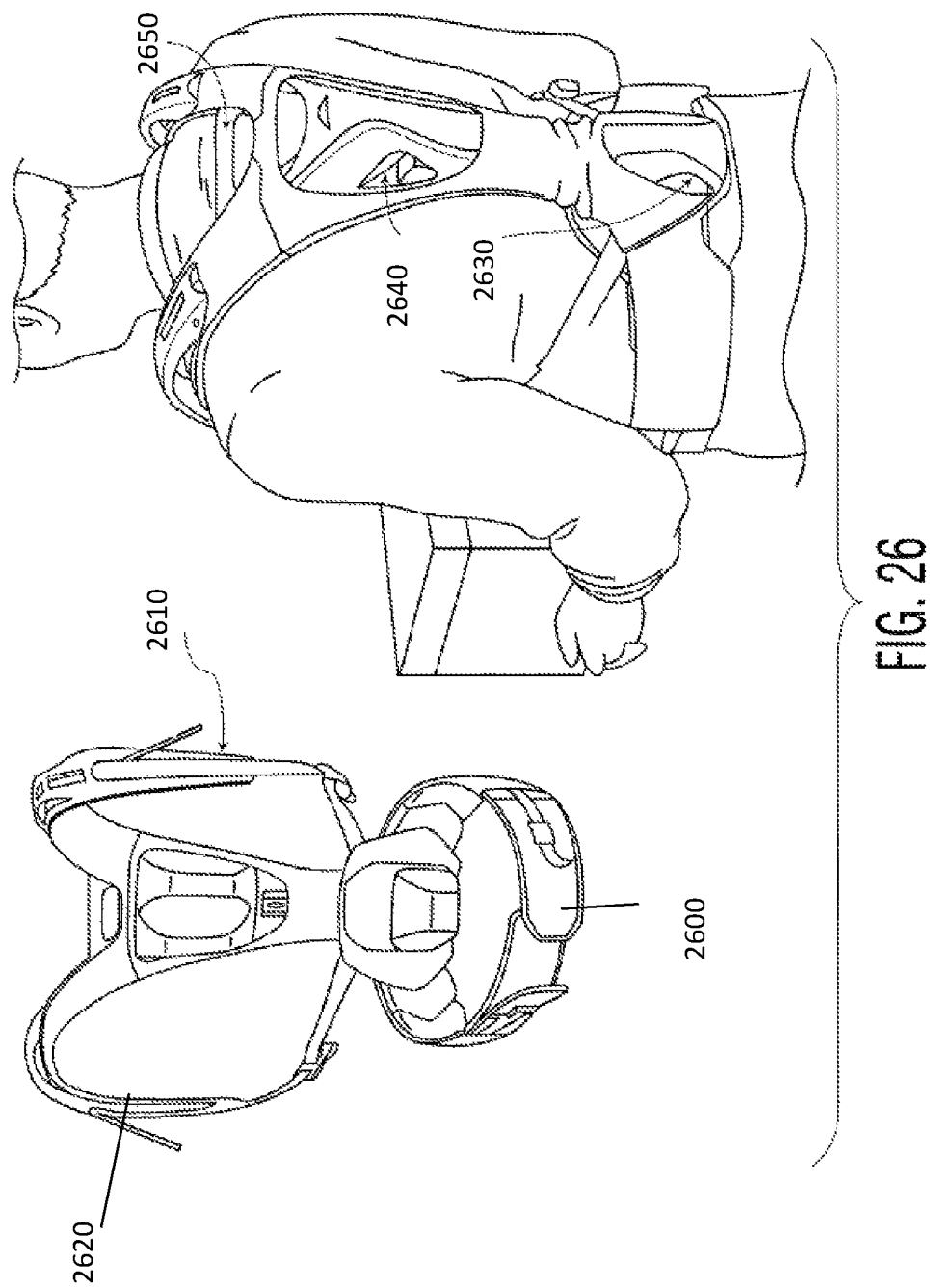
FIG. 26 provides a non-limiting prototype 2600 of a preferred embodiment of the present invention, including the prototype 2600 on its own (left panel) and the prototype 2600 worn by a user (right panel). As shown in the left panel, the shoulder straps 2610, 2620 taper toward their respective bottoms and have webbing that extends all the way to the top of the shoulder straps 2610, 2620. As shown in the right panel, the prototype includes a cutout 2630 in the bottom piece that echoes the cutout 2640 in the top piece. As shown in the right panel, the prototype 2600 includes a hook 2650.

Nothing in the present application is intended to limit the configuration(s) of the various components of the LV(SF) presented. Thus for example the figures provide embodiments in which cords are shown—Applicants note that this cordage is preferably Spectre™ 250-pound test, although other products are explicitly contemplated. Furthermore, although cords are shown, straps, chains or other LTM are contemplated. Similarly, the cord guides shown are merely illustrative of the generalized "cord guide means" contemplated, which may include rings (shown), channels, or other guide means as would be understood by one of ordinary skill in the art of such rigging. Similarly, the softvest shown in the CG figures and the softvest shown in FIG. 26 are two non-limiting configurations of the softvest, with other configurations explicitly contemplated.

With regard to the above, Applicants note that because of the possibility of friction in the routing of the cords/straps/etc. of the LTM, Applicants expressly contemplate various friction reducing methods for ensuring smooth motion of this aspect of the present invention, such as may be accomplished by, e.g., coated channel guides, pulleys, anti-friction coating(s), etc.

Hand Effector Means

Figure 8:
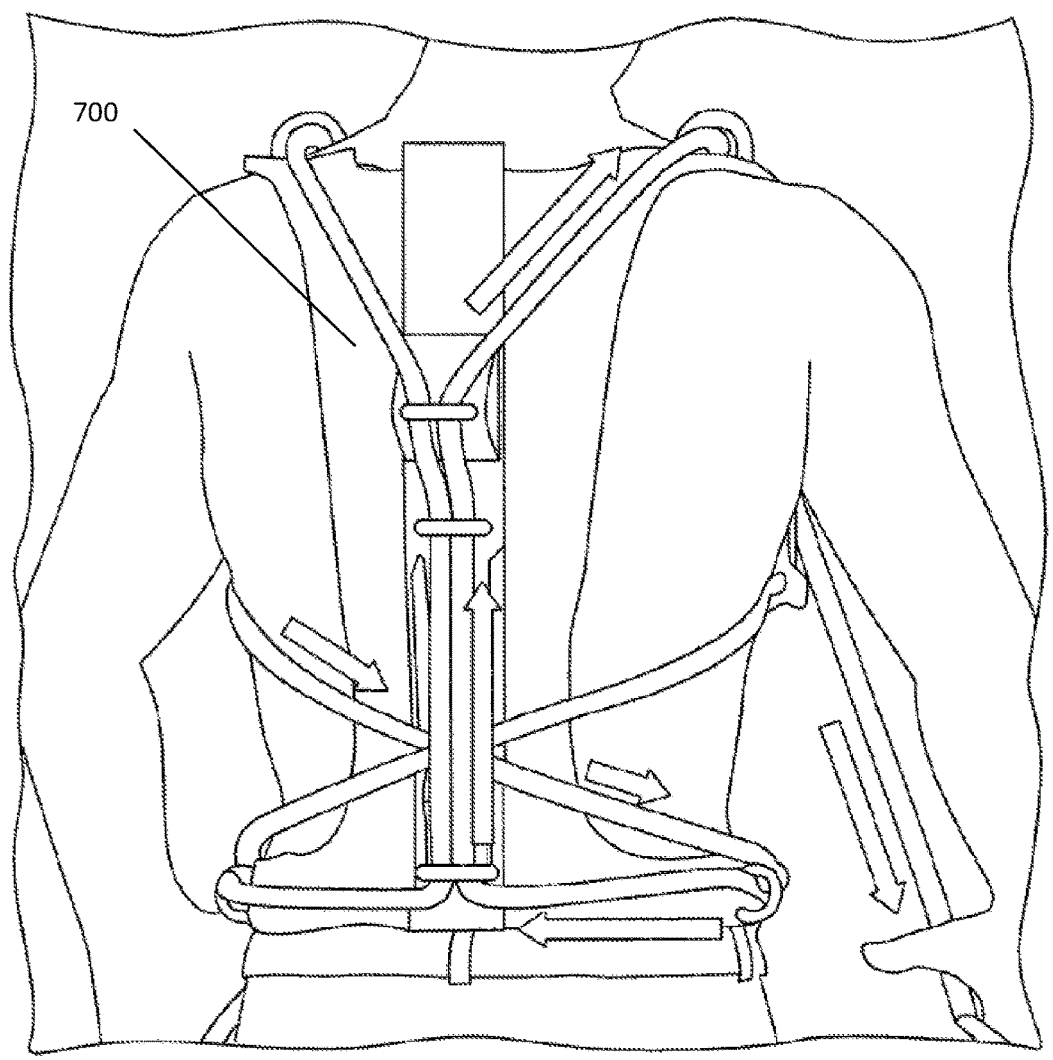
FIG. 8 provides the preferred LV(SF) of FIG. 7 with arrows added to indicate the direction of motion of the cordage beginning at the right hand as that hand is extended. Note that although the arrow immediately above the right hand appears to suggest a motion that is solely downward, in fact this motion is downward and forward. Note also that, although not shown in this figure, the motion of the cordage beginning at the left hand would be similar as the left hand is extended.
Figure 9:
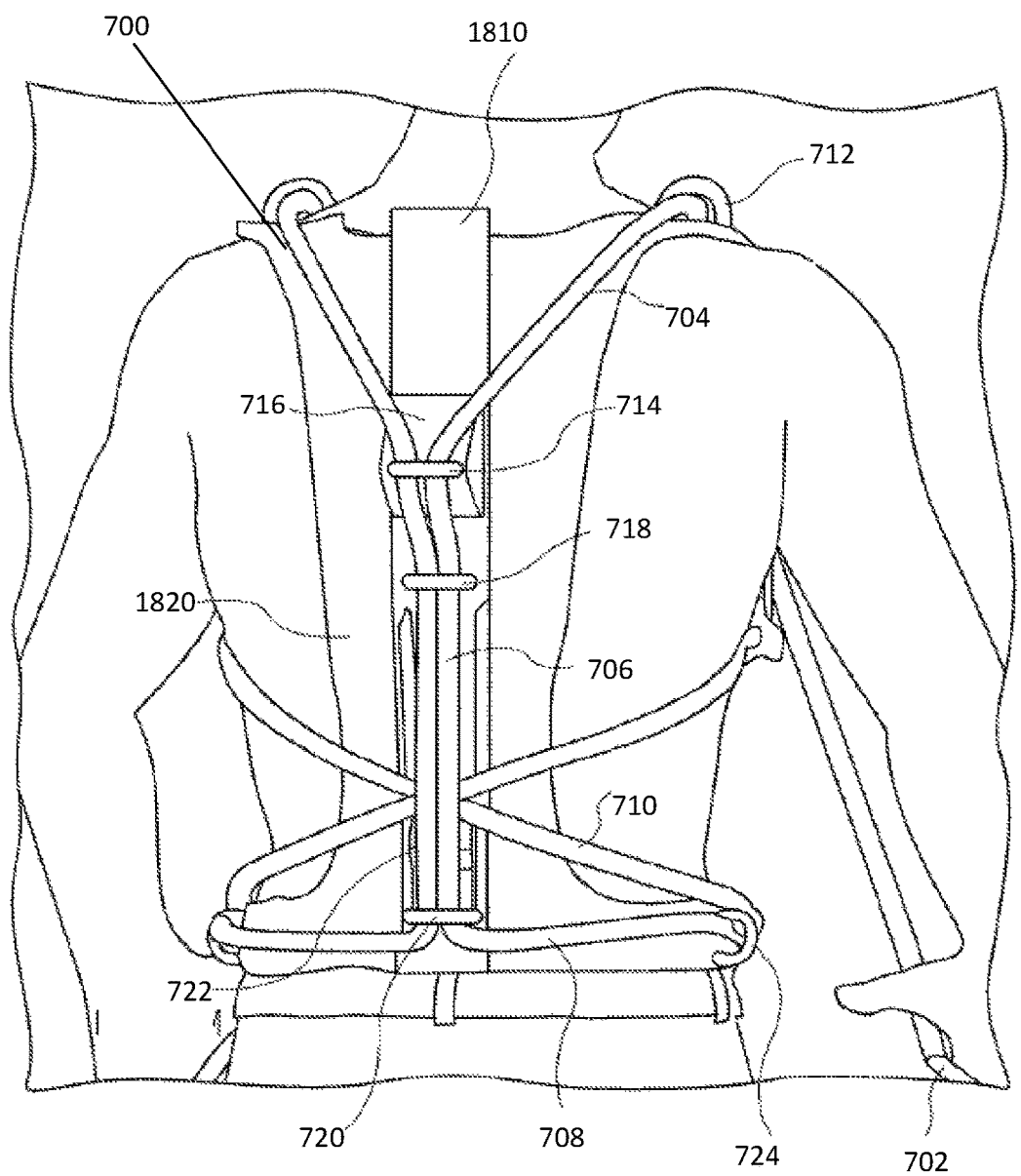
FIG. 9 provides the preferred LV(SF) of FIGS. 7-8 with the various components comprising this preferred embodiment 700 of the present invention labeled. Note that the "hand effector" portions 702 of this embodiment preferably comprise more than cord ends (see FIGS. 28-33 and text below); see text for further descriptions of various contemplated variations of the LV(SF) elements shown in this preferred embodiment. Note also that the labels "shoulder cord 704," "central cord 706," "waist cord 708" and "back cord 710" are typically used to refer to different regions of one continuous cord that, as shown in FIG. 8, preferably rises from hand, over the shoulder via a shoulder cord guide 712, down along the central back axis of the LV(SF) via an upper fulcrum cord guide 714 along an upper fulcrum 716, a central cord guide 718, and a lower fulcrum cord guide 720 along a lower fulcrum 722, across a portion of the waist via a waist cord guide 724, and then across the back to a terminating connector at the shoulder pad. Note that there are typically two such cords symmetrically disposed, although other configurations can be used.
Figure 10:
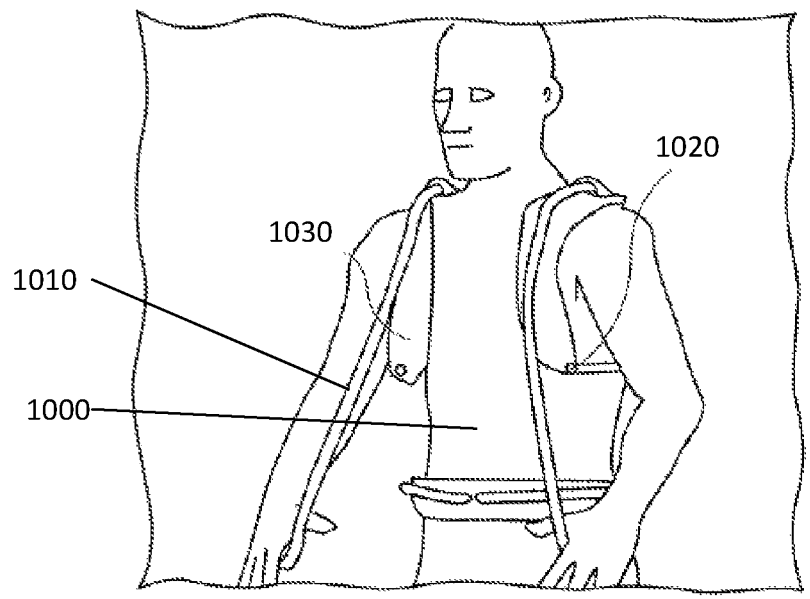
FIGS. 10-12 provides views of an alternative embodiment 1000 of the LV(SF) of the present invention. In this embodiment the back cords 1010 are in the "variant 1" ("VAR1") configuration, that is, horizontal from the cord connection point 1020 in each of the shoulder pads 1030 (see FIG. 10) around the torso and to the central cord guide in the backplate.
Figure 11:
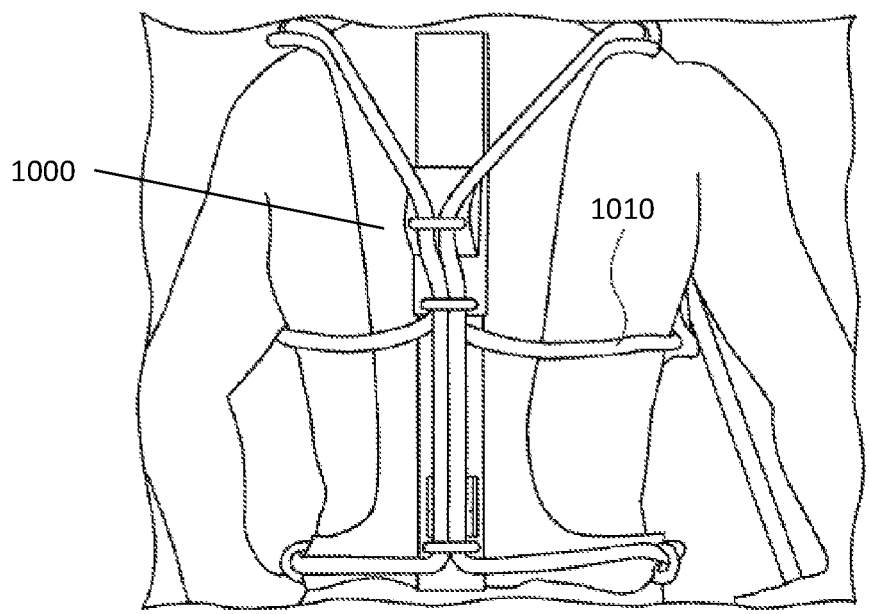
Figure 12:
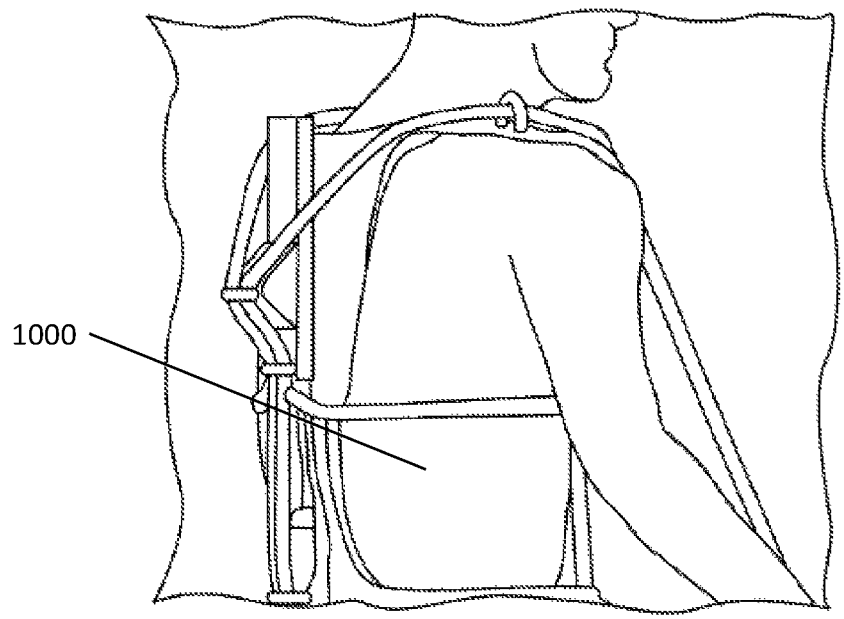
Figure 13:
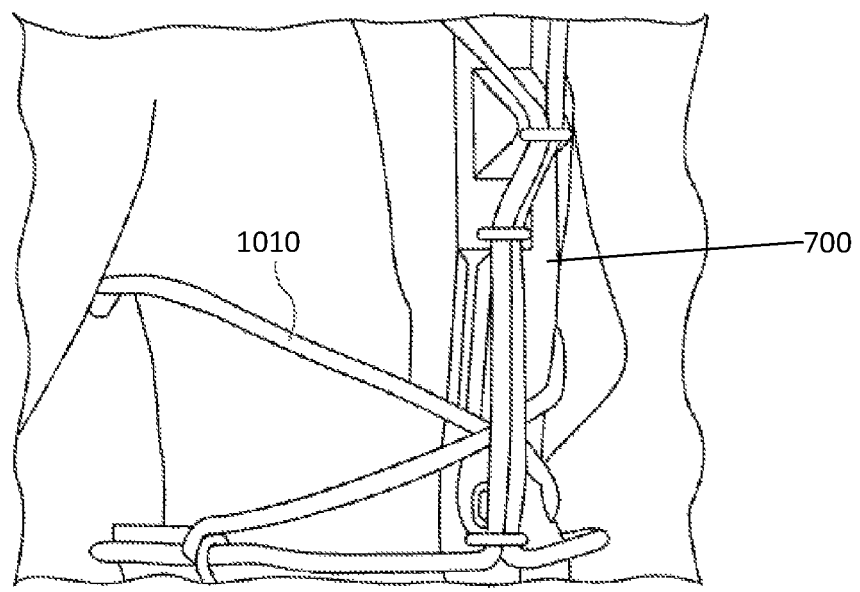
FIGS. 13-15 provide additional views of the preferred LV(SF) already shown in FIGS. 7-9. Note that in these figures the crossing point of the two back cords is schematic, and does not show in detail that the cords are not fused at this point, but rather cross one another. This caveat applies to other figures showing this preferred LV(SF) of the present invention.
Figure 14:
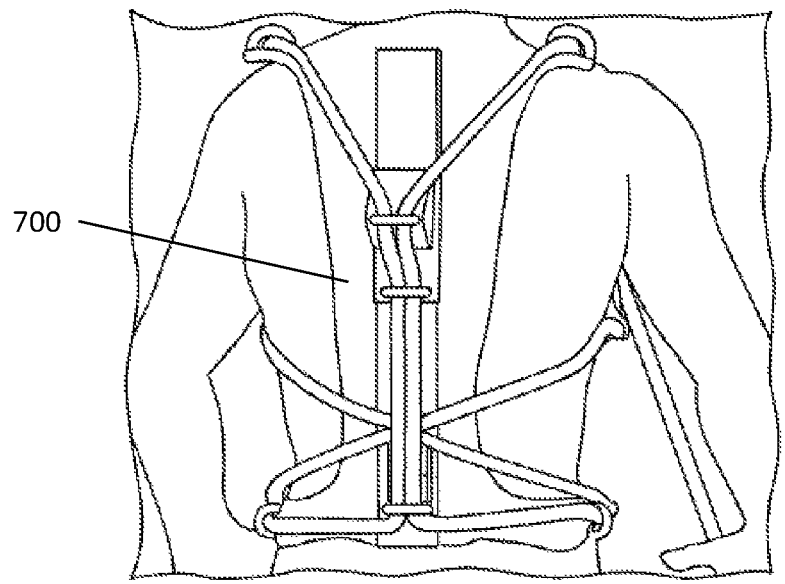
Figure 15:
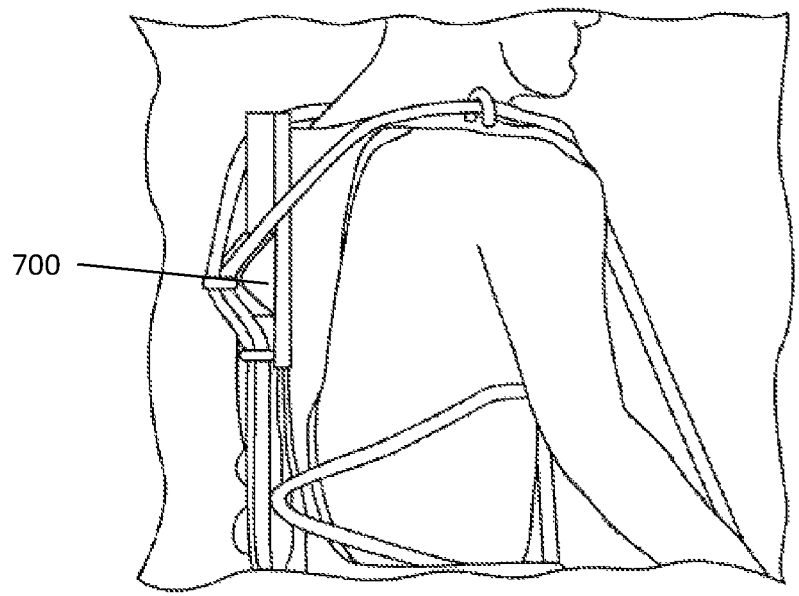
Figure 16:
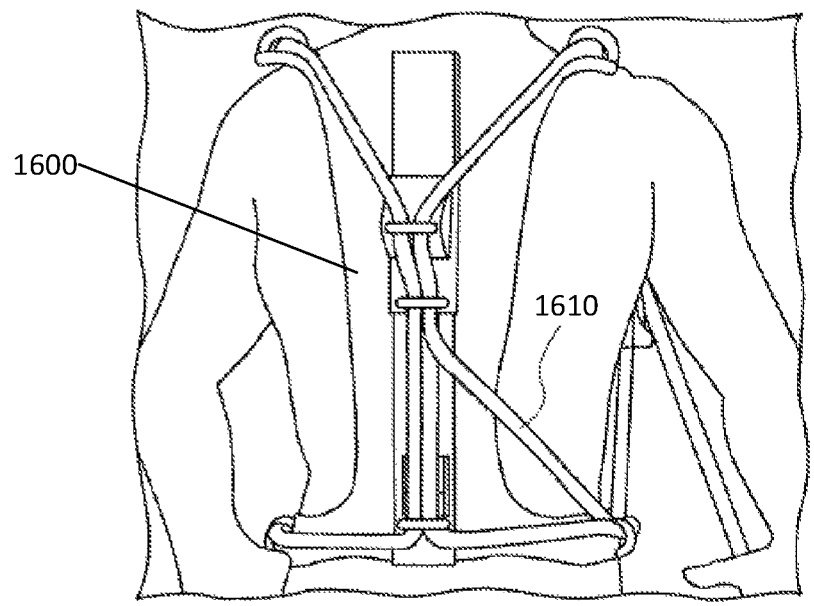
FIGS. 16-17 provides views of another of the alternative embodiment 1600 of the LV(SF) of the present invention. In this embodiment the back cords 1610 are in the "variant 2" ("VAR2") configuration, that is, descending from the cord connection point in each of the shoulder pads (see FIG. 10) down around the torso to the waist cord guide, and from there up to the central cord guide in the backplate. Note that FIGS. 16-17 show only the right back cord 1610, and that the left back cord (not shown) is symmetrically arranged.
Figure 17:
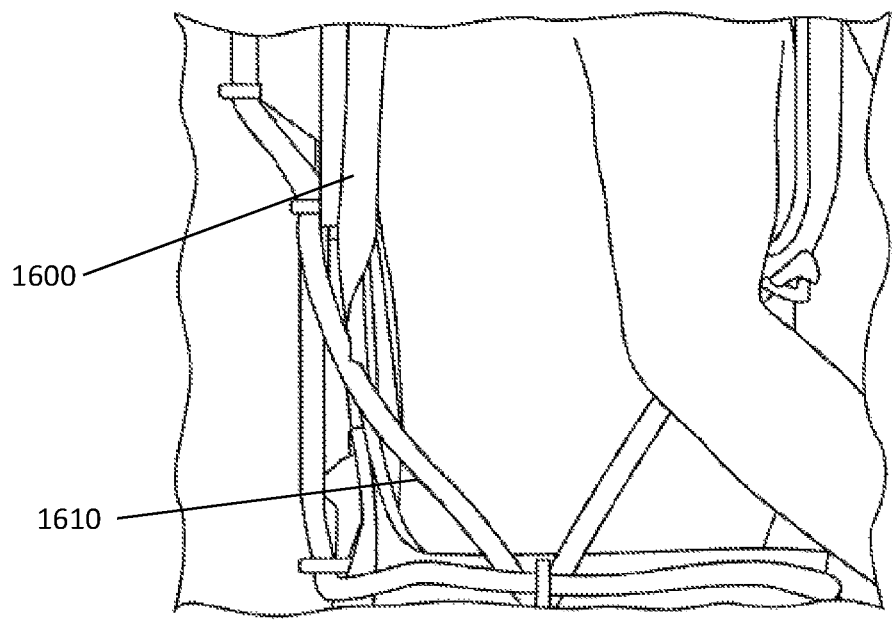
Figure 18:
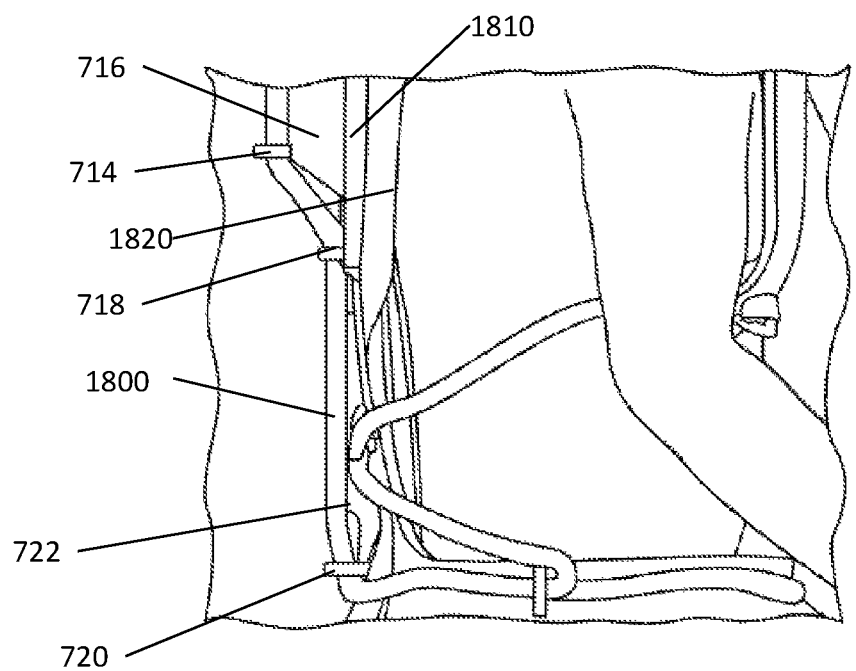
FIGS. 18-19 provide views of the preferred LV(SF) of the present invention, and particularly of the backplate assembly 1800 (including a backplate 1810, the upper fulcrum 716, the lower fulcrum 722, the upper fulcrum cord guide 714, the central cord guide 718, and the lower fulcrum cord guide 720) of this embodiment.
Figure 19:
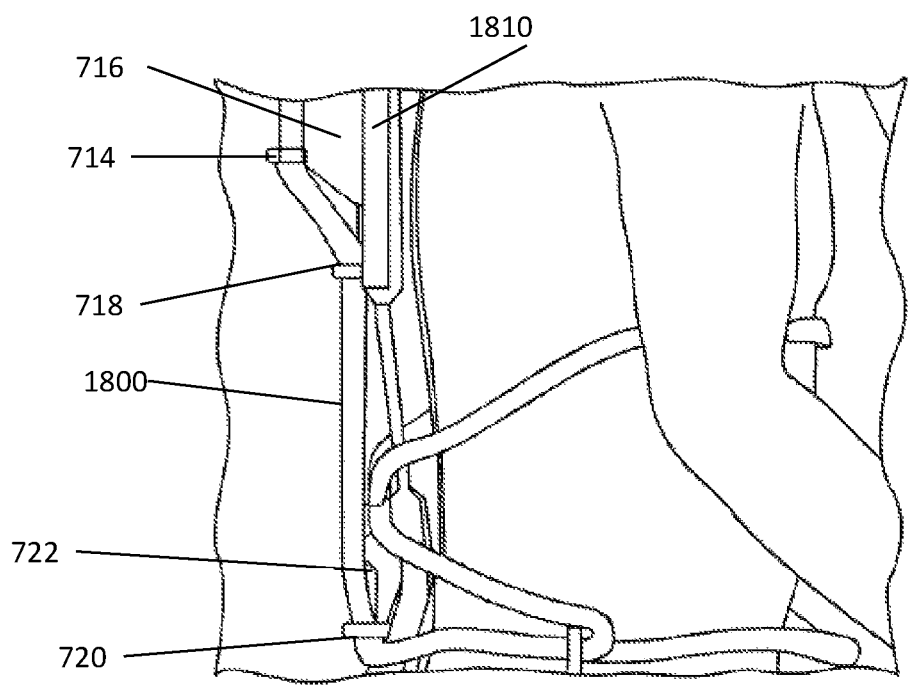

As shown in FIG. 9, the LV(SF) 700 of the present invention preferably comprises "Hand Effectors" ("HE") 702 or, more aptly, "Hand Effector Means," which provide a means for engaging the cords (or straps or chains or, most generally, LTM) of the LV(SF) present invention in such a way as to 1) allow free extension of the hand effector means 702 along the cords prior to a lift; and 2) lock/engage the hand effector means 702 on the cords during a lift so that the LV(SF) is engaged and the cords of the LV(SF) tighten in, e.g., the path shown in FIG. 8. Note that FIG. 9 merely shows the region of the hands in which the hand effector means 702 operate, not the hand effector means themselves.

Figure 29:
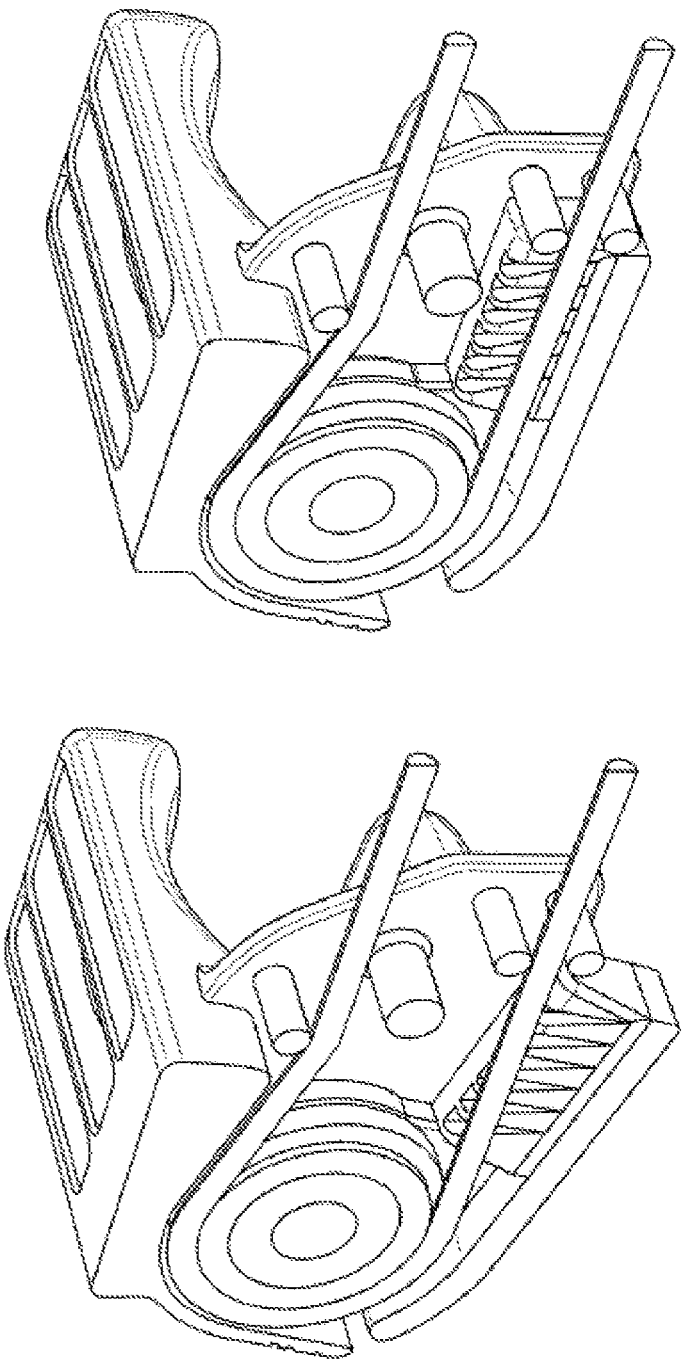
Figure 30:
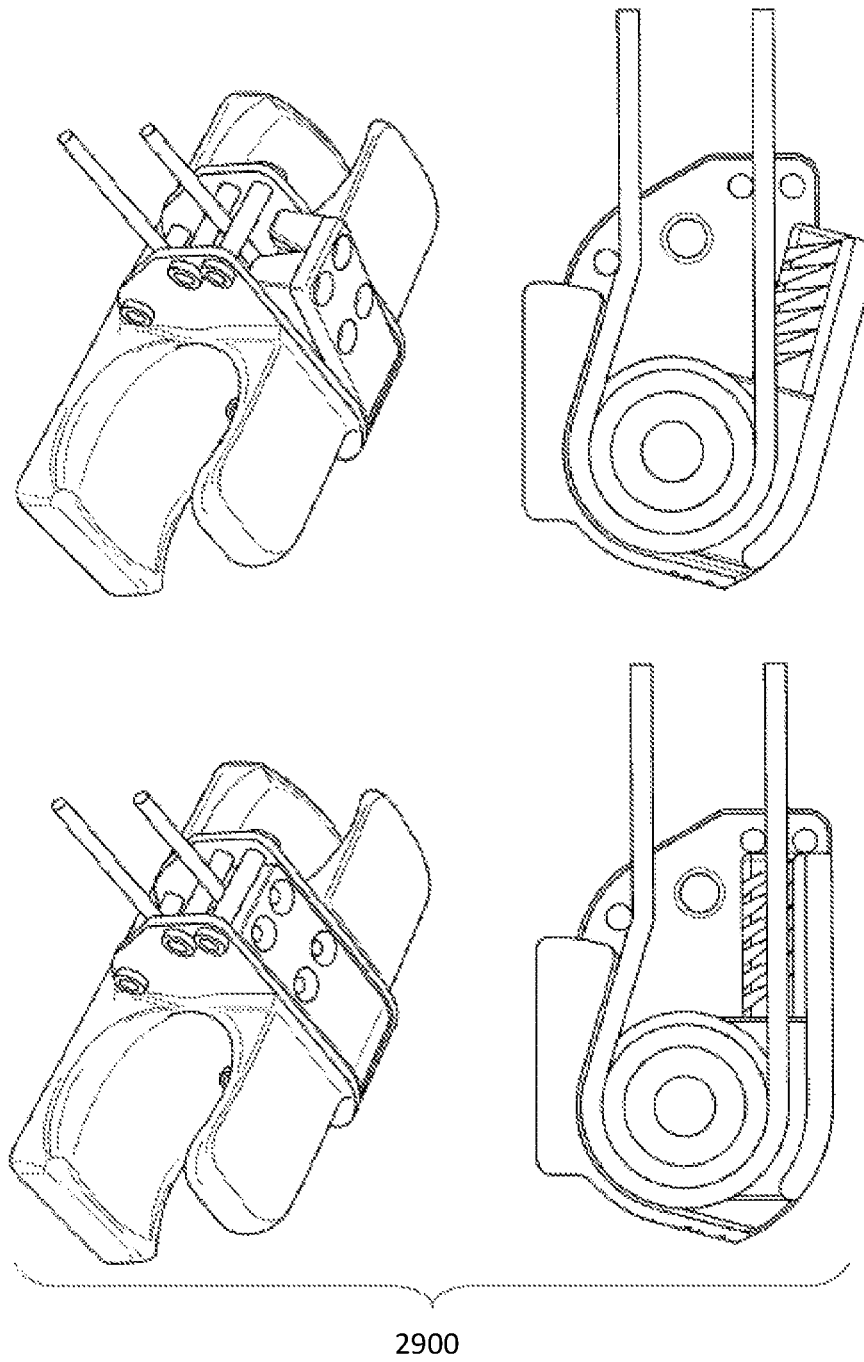
Figure 31:
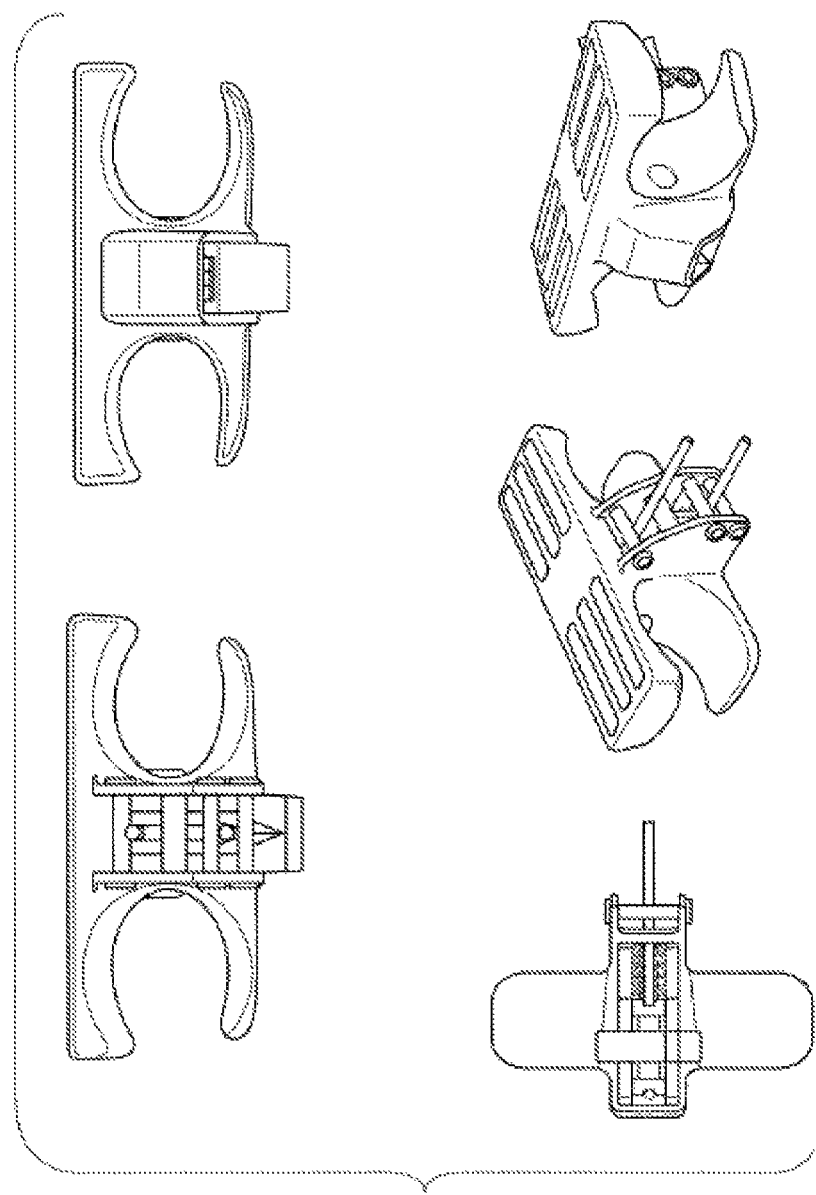
Figure 32:
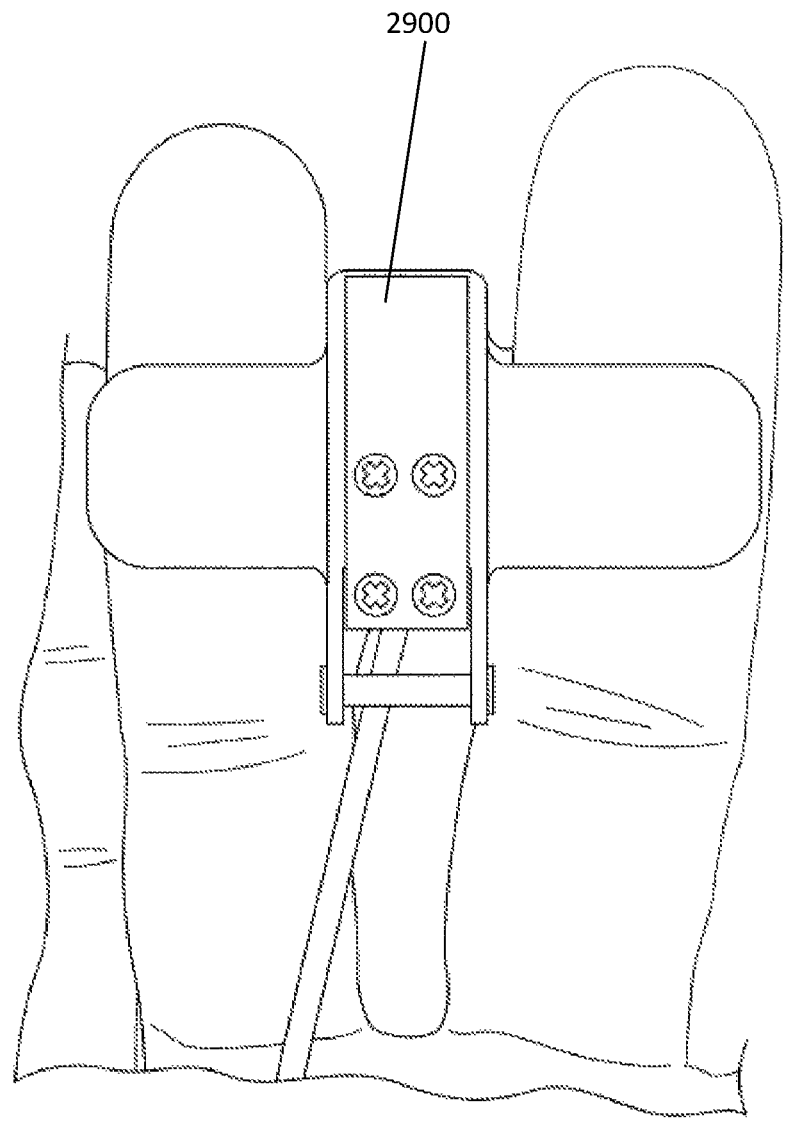
Figure 33:
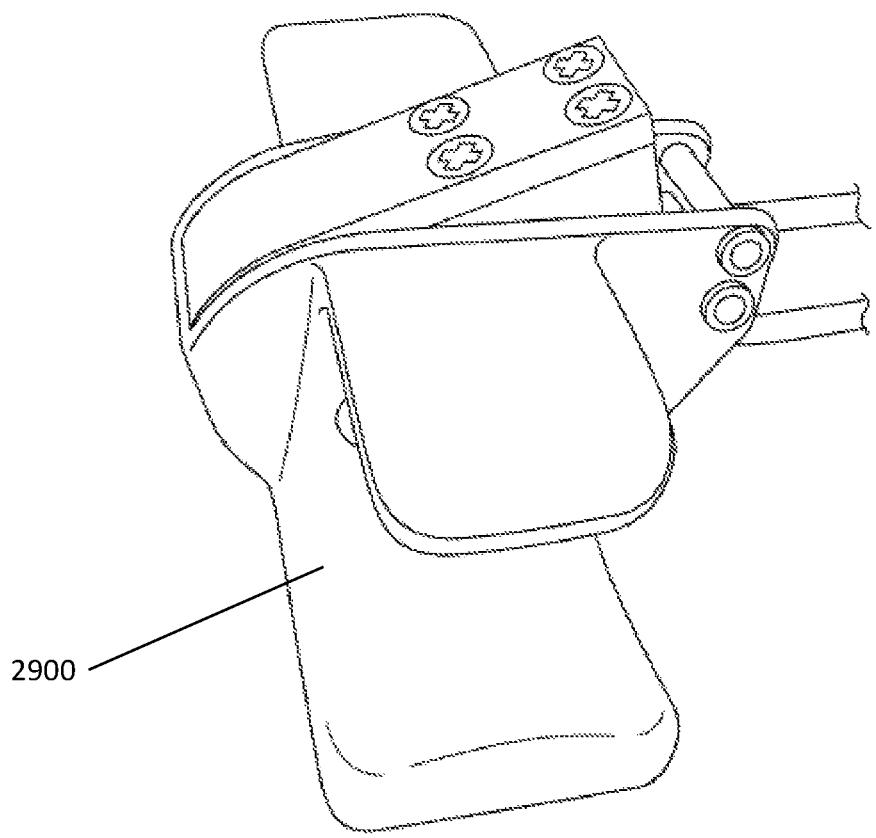

In this regard, the function of the LV(SF) of the present invention is intended to occur only upon lifting, and so the hand effector means must operate in a way that allows for free hand motion along the cords (LTM) when the LV(SF) is not intended to be engaged (i.e., when the wearer is not lifting), and alternately locks the cords (LTM) and thereby engages the LV(SF) when the wearer is lifting. FIGS. 28-33 provide non-limiting examples of a hand effector means that perform these two functions. FIGS. 29 and 30, for example, provide details of a hand effector means 2900 that is designed to be inserted over two fingers with minimal size and therefore minimal impedance of hand motion/function, a minimal impact that Applicants note is a preferred aspect of the present invention. In this figure, two configurations of the hand effector means 2900 are shown: the "open" configuration (shown to the left in FIG. 29 and to the top in FIG. 30) in which the toothed jaw of the hand effector means 2900 is not biting into the cord and therefore allows for free cord movement; and, the "closed" configuration (shown to the right in FIG. 29 and to the bottom in FIG. 30), in which this toothed jaw is closed on the cord and prevents cord slippage and, therefore, engages the action of the LV(SF). Applicants note that "toothed" as used above refers generically to an anti-slip surface internal to the hand effector means 2900 that can be in an engaged or disengaged position, and is explicitly not limited to teeth only.

Most generally, the hand effector means of the present invention is subject to at least the following design considerations: 1) minimal impact on hand function; and, 2) configuration in two-states, a disengaged state and an engaged state, where disengagement and engagement refers to unlocking/locking of the cord (LTM). Note that these requirements were not anticipated in advance, and are provided only in retrospect of the actual determination of these requirements of the hand effector means.

Medical Lifting Hand Effector Means

FIGS. 34-36 provide non-limiting examples of one embodiment 3400 of the medical lifting means of the present invention. As shown in these figures, this embodiment involves the use of lifting blades or paddle means 3410 that can be stowed (FIG. 34) or deployed (FIG. 35); and, when deployed, may be used in patient lifting (FIG. 36).

These blades/paddles 3410 are adapted for lifting in a number of ways, including but not limited to blade length, width, height, material, etc. Applicants contemplate various combinations of such parameters depending upon the exact medical lifting situation, patient physical health, weight, etc.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A support device comprising:
   a garment configured to be worn by a user, the garment including a back plate having an upper portion and a lower portion, the back plate configured and positioned to extend vertically along a central portion of a back of the user such that the upper portion of the back plate is proximate to an upper central portion of the back and the lower central portion of the back plate is proximate to a lower portion of the back when the garment is worn by the user;
   a pivot point located at the upper portion of the back plate; and
   at least one sensory feedback element coupled to the lower portion of the back plate, the at least one sensory feedback element configured to press into the back of the user in response to a non-ergonomic lifting posture by the user during a lifting operation, wherein the non-ergonomic lifting posture includes bending at the waist with a hunched back.

2. The device of claim 1, wherein the sensory feedback element is configured to encourage the user to adopt an ergonomic lifting posture during the lifting operation, wherein the ergonomic lifting posture comprises the user having a non-loaded curve of the spine.

3. The device of claim 1, wherein the sensory feedback element is configured to result in the user adopting the ergonomic lifting posture during at least 50% of lifting operations performed by the user.

4. The device of claim 1, further comprising a hand effector configured to allow free hand motion of the user relative to the device when the user is not performing the lifting operation, and configured to lock a motion of the user's hands relative to the device during the lifting operation.

5. The device of claim 1, wherein the at least one sensory feedback element includes a pad that is positioned so as to press into the back of the user in a region proximate L5 and S1 vertebrae of the user.

6. The device of claim 1, wherein the at least one sensory feedback element includes a pad that is positioned so as to press into the back of the user in a region proximate a T10 vertebra of the user.

7. The device of claim 1, wherein the at least one sensory feedback element includes a first pad that is positioned so as to press into the back of the user in a region proximate L5 and S1 vertebrae of the user and a second pad that is positioned so as to press into the back of the user in a region proximate a T10 vertebra of the user.

8. A lifting vest configured to provide sensory feedback, the lifting vest comprising:
   a back plate configured and positioned to extend vertically along a central portion of a back of a user when the lifting vest is worn by the user;
   a load transfer element configured to transfer a weight of a load from a location of the load to a point over shoulders of the user and down to a lower torso of the user;
   a posture compliance element configured to passively or actively enforce an ergonomic back posture;
   a coupling device configured to connect the load transfer element to the postural compliance element; and
   at least one sensory feedback element coupled to the back plate, the at least one sensory feedback element configured to press into the back of the user in response to a non-ergonomic lifting posture by the user during a lifting operation, wherein the non-ergonomic lifting posture includes bending at the waist with a hunched back.

9. The lifting vest of claim 8, where the at least one sensory feedback element is integrated into the posture compliance element.

10. The lifting vest of claim 8, wherein the sensory feedback element is configured to result in the user adopting an ergonomic lifting posture during at least 50% of lifting operations performed by the user.

11. The lifting vest of claim 8, further comprising a hand effector configured to allow free hand motion of the user relative to the load transfer element when the user is not performing the lifting operation, and configured to lock a motion of the user's hands relative to the load transfer element during a lifting operation.

12. The lifting vest of claim 8, wherein the at least one sensory feedback element includes a pad that is positioned so as to press into the back of the user in a region proximate L5 and S1 vertebrae of the user.

13. The lifting vest of claim 8, wherein the at least one sensory feedback element includes a pad that is positioned so as to press into the back of the user in a region proximate a T10 vertebra of the user.

14. The lifting vest of claim 8, wherein the at least one sensory feedback element includes a first pad that is positioned so as to press into the back of the user in a region proximate L5 and S1 vertebrae of the user and a second pad that is positioned so as to press into the back of the user in a region proximate a T10 vertebra of the user.

15. A method of creating appropriate lifting posture in an individual, the method comprising enabling the individual to perform a lifting operation while wearing the support device of claim 1.

16. A method of creating appropriate lifting posture in an individual, the method comprising enabling the individual to perform a lifting operation while wearing the lifting vest of claim 8.

\* \* \* \* \*